US011963796B1

(12) United States Patent
Windmiller et al.

(10) Patent No.: US 11,963,796 B1
(45) Date of Patent: Apr. 23, 2024

(54) HETEROGENEOUS INTEGRATION OF SILICON-FABRICATED SOLID MICRONEEDLE SENSORS AND CMOS CIRCUITRY

(71) Applicant: Biolinq Incorporated, San Diego, CA (US)

(72) Inventors: Joshua Windmiller, San Diego, CA (US); Jared Rylan Tangney, Encinitas, CA (US)

(73) Assignee: Biolinq Incorporated, San Diego, CA (US)

( * ) Notice: Subject to any disclaimer, the term of this patent is extended or adjusted under 35 U.S.C. 154(b) by 414 days.

(21) Appl. No.: 17/349,234

(22) Filed: Jun. 16, 2021

Related U.S. Application Data

(63) Continuation of application No. 15/961,793, filed on Apr. 24, 2018, now Pat. No. 11,045,142.

(Continued)

(51) Int. Cl.
*A61B 5/00* (2006.01)
*A61M 37/00* (2006.01)

(52) U.S. Cl.
CPC ............ *A61B 5/685* (2013.01); *A61B 5/0048* (2013.01); *A61M 37/0015* (2013.01); *A61M 2037/0046* (2013.01)

(58) Field of Classification Search
CPC .............. A61B 5/6833; A61B 5/14514; A61B 5/14517; A61B 5/14532; A61B 5/14539;

(Continued)

(56) References Cited

U.S. PATENT DOCUMENTS 4,305,401 A 12/1981 Reissmueller et al.
4,323,996 A 4/1982 Ganter
(Continued)

FOREIGN PATENT DOCUMENTS

CN 101068591 A 11/2007
CN 112617822 A 4/2021
(Continued)

OTHER PUBLICATIONS

Abbot press release (2020). "New late-breaking data show use of abbott's Freestyle® Libre System significantly reduces HBA1C levels in people with type 2 diabetes using insulin or not," 3 pages.
(Continued)

*Primary Examiner* — Eric J Messersmith
(74) *Attorney, Agent, or Firm* — Cooley LLP (57) ABSTRACT

A skin-adorned physiological or biochemical sensing device is disclosed herein. The device preferably comprises a first substrate and a second substrate. The first substrate comprises an array of solid microneedles designed to penetrate a biological interface to access a physiological fluid or tissue. Each microneedle is capable of electrical interface with the physiological fluid or tissue. The second substrate comprises integrated circuitry designed to transduce at least one signal produced by an electrophysiological or electrochemical reaction. A sensing device is formed that is capable of interpreting the signal arising from the electrophysiological or electrochemical reaction to ascertain the level of some physiological or biochemical entity.

21 Claims, 4 Drawing Sheets

Related U.S. Application Data (60) Provisional application No. 62/492,142, filed on Apr. 29, 2017.

(58) Field of Classification Search
CPC . A61B 5/14546; A61B 5/1477; A61B 5/1486; A61B 5/14865; A61B 5/150022; A61B 5/150267; A61B 5/150442; A61B 5/150969; A61B 5/150984; A61B 5/685; A61M 37/0015; B32B 2255/12; B32B 2307/202; B32B 2307/206; B32B 2311/02; B32B 2323/04; B32B 2367/00; B32B 2383/00; B32B 2405/00; B32B 2556/00; B32B 37/1284; B32B 38/10; B32B 38/145; Y10T 156/10
See application file for complete search history.

(56) References Cited

U.S. PATENT DOCUMENTS

| | | | |
|---|---|---|---|
| 4,407,295 A | 10/1983 | Steuer et al. |
| 4,450,842 A | 5/1984 | Zick et al. |
| 4,908,117 A | 3/1990 | Kinlen et al. |
| 4,969,468 A | 11/1990 | Byers et al. |
| 5,035,711 A | 7/1991 | Aoki et al. |
| 5,131,390 A | 7/1992 | Sakaguchi et al. |
| 5,279,543 A | 1/1994 | Glikfeld et al. |
| 5,286,364 A | 2/1994 | Yacynych et al. |
| 5,540,828 A | 7/1996 | Yacynych |
| 5,730,714 A | 3/1998 | Guy et al. |
| 5,766,132 A | 6/1998 | Yasukawa et al. |
| 5,832,410 A | 11/1998 | Lin et al. |
| 5,869,078 A | 2/1999 | Baudino |
| 5,953,306 A | 9/1999 | Yi |
| 6,036,055 A | 3/2000 | Mogadam et al. |
| 6,091,975 A | 7/2000 | Daddona et al. |
| 6,132,449 A | 10/2000 | Lum et al. |
| 6,132,499 A | 10/2000 | Wong et al. |
| 6,132,755 A | 10/2000 | Eicher et al. |
| 6,139,718 A | 10/2000 | Kurnik et al. |
| 6,269,053 B1 | 7/2001 | Kawata et al. |
| 6,284,126 B1 | 9/2001 | Kurnik et al. |
| 6,364,890 B1 | 4/2002 | Lum et al. |
| 6,413,396 B1 | 7/2002 | Yang et al. |
| 6,465,091 B1 | 10/2002 | Ou-yang |
| 6,471,903 B2 | 10/2002 | Sherman et al. |
| 6,527,762 B1 | 3/2003 | Santini, Jr. et al. |
| 6,551,849 B1 | 4/2003 | Kenney |
| 6,587,705 B1 | 7/2003 | Kim et al. |
| 6,599,408 B1 | 7/2003 | Chan et al. |
| 6,603,987 B2 | 8/2003 | Whitson |
| 6,611,707 B1 | 8/2003 | Prausnitz et al. |
| 6,793,789 B2 | 9/2004 | Choi et al. |
| 6,801,041 B2 | 10/2004 | Karinka et al. |
| 6,814,845 B2 | 11/2004 | Wilson et al. |
| 6,862,466 B2 | 3/2005 | Ackerman |
| 6,908,453 B2 | 6/2005 | Fleming et al. |
| 7,081,195 B2 | 7/2006 | Simpson et al. |
| 7,097,776 B2 | 8/2006 | Govinda Raju |
| 7,132,054 B1 | 11/2006 | Kravitz et al. |
| 7,262,068 B2 | 8/2007 | Roy et al. |
| 7,343,188 B2 | 3/2008 | Sohrab |
| 7,344,499 B1 | 3/2008 | Prausnitz et al. |
| 7,366,556 B2 | 4/2008 | Brister et al. |
| 7,415,299 B2 | 8/2008 | Zimmermann et al. |
| 7,429,333 B2 | 9/2008 | Chiou et al. |
| 7,456,112 B2 | 11/2008 | Lee |
| 7,471,972 B2 | 12/2008 | Rhodes et al. |
| 7,473,244 B2 | 1/2009 | Frazier et al. |
| 7,493,232 B1 | 2/2009 | Surina |
| 7,534,330 B2 | 5/2009 | Yu et al. |
| 7,583,990 B2 | 9/2009 | Goode, Jr. |
| 7,599,726 B2 | 10/2009 | Goode, Jr. |
| 7,613,491 B2 | 11/2009 | Boock |
| 7,645,263 B2 | 1/2010 | Angel et al. |
| 7,715,893 B2 | 5/2010 | Kamath et al. |
| 7,768,408 B2 | 8/2010 | Reggiardo et al. |
| 7,778,680 B2 | 8/2010 | Goode, Jr. |
| 7,797,028 B2 | 9/2010 | Goode, Jr. |
| 7,811,231 B2 | 10/2010 | Jin et al. |
| 7,837,654 B2 | 11/2010 | Shumate et al. |
| 7,885,697 B2 | 2/2011 | Brister et al. |
| 7,905,833 B2 | 3/2011 | Brister et al. |
| 7,917,186 B2 | 3/2011 | Kamath et al. |
| 7,949,382 B2 | 5/2011 | Jina |
| 7,959,569 B2 | 6/2011 | Goode et al. |
| 8,005,526 B2 | 8/2011 | Martin et al. |
| 8,010,174 B2 | 8/2011 | Goode, Jr. |
| 8,022,292 B2 | 9/2011 | Arianpour et al. |
| 8,064,977 B2 | 11/2011 | Boock et al. |
| 8,088,321 B2 | 1/2012 | Ferguson et al. |
| 8,094,009 B2 | 1/2012 | Allen et al. |
| 8,108,023 B2 | 1/2012 | Mir et al. |
| 8,110,079 B2 | 2/2012 | Gooding et al. |
| 8,125,331 B2 | 2/2012 | Allen et al. |
| 8,130,095 B2 | 3/2012 | Allen et al. |
| 8,160,665 B2 | 4/2012 | Mischler et al. |
| 8,160,671 B2 | 4/2012 | Kamath et al. |
| 8,160,834 B2 | 4/2012 | Liang et al. |
| 8,162,901 B2 | 4/2012 | Gonnelli et al. |
| RE43,399 E | 5/2012 | Simpson et al. |
| 8,216,138 B1 | 7/2012 | McGarraugh |
| 8,236,368 B2 | 8/2012 | Jung et al. |
| 8,249,684 B2 | 8/2012 | Kamath et al. |
| 8,257,324 B2 | 9/2012 | Prausnitz et al. |
| 8,280,475 B2 | 10/2012 | Brister et al. |
| 8,280,476 B2 | 10/2012 | Jina |
| 8,284,046 B2 | 10/2012 | Allen et al. |
| 8,287,453 B2 | 10/2012 | Li et al. |
| 8,308,960 B2 | 11/2012 | Kälvesten et al. |
| 8,346,335 B2 | 1/2013 | Harper et al. |
| 8,376,945 B2 | 2/2013 | Hayter et al. |
| 8,386,004 B2 | 2/2013 | Kamath et al. |
| 8,423,114 B2 | 4/2013 | Simpson et al. |
| 8,428,678 B2 | 4/2013 | Kamath et al. |
| 8,452,369 B2 * | 5/2013 | Huys ............... G01N 33/48728 600/372 |
| 8,463,350 B2 | 6/2013 | Kamath et al. |
| 8,483,793 B2 | 7/2013 | Simpson et al. |
| 8,506,529 B1 | 8/2013 | Yang |
| 8,548,553 B2 | 10/2013 | Kamath et al. |
| 8,565,848 B2 | 10/2013 | Brister et al. |
| 8,574,165 B2 | 11/2013 | Marsh |
| 8,617,069 B2 | 12/2013 | Bernstein et al. |
| RE44,695 E | 1/2014 | Simpson et al. |
| 8,626,257 B2 | 1/2014 | Li et al. |
| 8,637,351 B2 | 1/2014 | Kälvesten et al. |
| 8,660,628 B2 | 2/2014 | Wang et al. |
| 8,708,966 B2 | 4/2014 | Allen et al. |
| 8,798,799 B2 | 8/2014 | Deo et al. |
| 8,815,070 B2 | 8/2014 | Wang et al. |
| 8,870,763 B2 | 10/2014 | Yang et al. |
| 8,882,665 B2 | 11/2014 | Yang et al. |
| 9,008,743 B2 | 4/2015 | Hayter et al. |
| 9,008,745 B2 | 4/2015 | Pushpala et al. |
| 9,055,901 B2 | 6/2015 | Brister et al. |
| 9,125,625 B2 | 9/2015 | Wang et al. |
| 9,182,368 B2 | 11/2015 | Pushpala et al. |
| 9,234,872 B2 | 1/2016 | Homyk et al. |
| 9,248,273 B2 | 2/2016 | Guvanasen et al. |
| 9,332,934 B2 | 5/2016 | Hayter et al. |
| 9,336,423 B2 | 5/2016 | Goodnow et al. |
| 9,357,951 B2 | 6/2016 | Simpson et al. |
| 9,386,954 B2 | 7/2016 | Saini et al. |
| 9,387,000 B2 | 7/2016 | Corrie et al. |
| 9,414,778 B2 | 8/2016 | Mao et al. |
| 9,420,965 B2 | 8/2016 | Brauker et al. |
| 9,532,741 B2 | 1/2017 | Brauker et al. |
| 9,551,698 B2 | 1/2017 | Huys et al. |
| 9,662,056 B2 | 5/2017 | Budiman et al. |
| 9,737,247 B2 | 8/2017 | Wang et al. |
| 9,743,870 B2 | 8/2017 | Wang et al. |
| 9,743,871 B2 | 8/2017 | Simpson et al. |
| 9,757,061 B2 | 9/2017 | Shults et al. |

(56) References Cited

U.S. PATENT DOCUMENTS

| | | |
|---|---|---|
| 9,770,211 B2 | 9/2017 | Hayter et al. |
| 9,804,114 B2 | 10/2017 | Rhodes et al. |
| 9,933,387 B1 | 4/2018 | McCanna et al. |
| 9,958,409 B2 | 5/2018 | Gerber et al. |
| 10,022,076 B2 | 7/2018 | Hoss et al. |
| 10,039,480 B2 | 8/2018 | Brauker et al. |
| 10,046,114 B1 | 8/2018 | Biederman et al. |
| 10,052,055 B2 | 8/2018 | Li et al. |
| 10,092,207 B1 | 10/2018 | Windmiller |
| 10,136,846 B2 | 11/2018 | Wang et al. |
| 10,173,042 B2 | 1/2019 | Pushpala et al. |
| 10,182,748 B2 | 1/2019 | Catt et al. |
| 10,188,333 B2 | 1/2019 | Kamath et al. |
| 10,228,341 B2 | 3/2019 | Katsuki et al. |
| 10,299,712 B2 | 5/2019 | Brister et al. |
| 10,327,678 B2 | 6/2019 | Gottlieb et al. |
| 10,492,708 B1 | 12/2019 | Windmiller |
| D875,254 S | 2/2020 | Cooke et al. |
| 10,549,080 B2 | 2/2020 | Pushpala et al. |
| 10,610,103 B2 | 4/2020 | Brister et al. |
| 10,709,332 B2 | 7/2020 | Brister et al. |
| 10,743,800 B2 | 8/2020 | Larvenz et al. |
| 10,820,860 B2 | 11/2020 | Pushpala et al. |
| 10,881,334 B2 | 1/2021 | Facchinetti et al. |
| 10,932,700 B2 | 3/2021 | Simpson et al. |
| 10,983,083 B2 | 4/2021 | Harding et al. |
| 11,020,026 B2 | 6/2021 | Boock et al. |
| 11,035,872 B2 | 6/2021 | Boutelle et al. |
| 11,045,142 B1 | 6/2021 | Windmiller et al. |
| 11,051,724 B2 | 7/2021 | Pace et al. |
| 11,123,532 B2 | 9/2021 | Pushpala et al. |
| 11,179,068 B2 | 11/2021 | Pace et al. |
| 11,197,985 B2 | 12/2021 | Pushpala et al. |
| 11,272,866 B2 | 3/2022 | Pushpala et al. |
| 11,272,885 B2 | 3/2022 | Pushpala et al. |
| 11,291,390 B2 | 4/2022 | Pushpala et al. |
| 11,331,022 B2 | 5/2022 | Halac et al. |
| 11,359,300 B1 | 6/2022 | Beer et al. |
| 11,406,818 B2 | 8/2022 | Windmiller |
| 11,478,194 B2 | 10/2022 | Windmiller et al. |
| 11,596,332 B2 | 3/2023 | Shults et al. |
| 11,654,270 B2 | 5/2023 | Mansfield, III et al. |
| D988,160 S | 6/2023 | Morelock |
| 11,672,965 B2 | 6/2023 | Mansfield, III et al. |
| 2002/0004640 A1 | 1/2002 | Conn et al. |
| 2002/0020688 A1 | 2/2002 | Sherman et al. |
| 2002/0055704 A1 | 5/2002 | Scott et al. |
| 2002/0072784 A1 | 6/2002 | Norman, Jr. et al. |
| 2002/0105080 A1 | 8/2002 | Speakman |
| 2002/0187556 A1 | 12/2002 | Shartle et al. |
| 2003/0088166 A1 | 5/2003 | Say et al. |
| 2003/0095582 A1 | 5/2003 | Ackley |
| 2003/0100040 A1 | 5/2003 | Bonnecaze et al. |
| 2003/0104119 A1 | 6/2003 | Wilson et al. |
| 2003/0135158 A1 | 7/2003 | Gonnelli |
| 2003/0208167 A1 | 11/2003 | Prausnitz et al. |
| 2003/0225360 A1 | 12/2003 | Eppstein et al. |
| 2003/0235817 A1 | 12/2003 | Bartkowiak et al. |
| 2004/0065158 A1 | 4/2004 | Schrepfer et al. |
| 2004/0082875 A1 | 4/2004 | Donoghue et al. |
| 2004/0220625 A1 | 11/2004 | Silvestri et al. |
| 2005/0036020 A1 | 2/2005 | Li et al. |
| 2005/0137536 A1 | 6/2005 | Gonnelli |
| 2005/0209565 A1 | 9/2005 | Yuzhakov et al. |
| 2005/0267440 A1 | 12/2005 | Herman et al. |
| 2005/0272989 A1 | 12/2005 | Shah et al. |
| 2006/0015061 A1 | 1/2006 | Kuo et al. |
| 2006/0016700 A1 | 1/2006 | Brister et al. |
| 2006/0173259 A1 | 8/2006 | Flaherty et al. |
| 2006/0264716 A1 | 11/2006 | Zander |
| 2006/0281121 A1 | 12/2006 | Unger et al. |
| 2007/0078445 A1 | 4/2007 | Malloy |
| 2007/0169533 A1 | 7/2007 | Shah et al. |
| 2007/0170054 A2 | 7/2007 | Wilsey |
| 2007/0213044 A1 | 9/2007 | Steingart et al. |
| 2007/0282246 A1 | 12/2007 | Henley |
| 2008/0009800 A1 | 1/2008 | Nickel |
| 2008/0009801 A1 | 1/2008 | Nickel |
| 2008/0027369 A1 | 1/2008 | Carter et al. |
| 2008/0033269 A1 | 2/2008 | Zhang |
| 2008/0097280 A1 | 4/2008 | Martin et al. |
| 2008/0097352 A1 | 4/2008 | Beck et al. |
| 2008/0119707 A1 | 5/2008 | Stafford |
| 2008/0154107 A1 | 6/2008 | Jina |
| 2008/0156661 A1 | 7/2008 | Cooper et al. |
| 2008/0213461 A1 | 9/2008 | Gill et al. |
| 2008/0221408 A1 | 9/2008 | Hoarau et al. |
| 2008/0234562 A1 | 9/2008 | Jina |
| 2008/0255434 A1 | 10/2008 | Hayter et al. |
| 2008/0275327 A1 | 11/2008 | Faarbaek et al. |
| 2009/0057148 A1 | 3/2009 | Wieder et al. |
| 2009/0066348 A1 | 3/2009 | Shin et al. |
| 2009/0069651 A1 | 3/2009 | Zimmermann et al. |
| 2009/0069697 A1 | 3/2009 | Frazier et al. |
| 2009/0084678 A1 | 4/2009 | Joshi et al. |
| 2009/0088652 A1 | 4/2009 | Tremblay |
| 2009/0090623 A1 | 4/2009 | Chuang et al. |
| 2009/0099427 A1 | 4/2009 | Jina et al. |
| 2009/0101498 A1 | 4/2009 | Papadimitrakopoulos et al. |
| 2009/0131778 A1 | 5/2009 | Jina et al. |
| 2009/0143761 A1 | 6/2009 | Cantor et al. |
| 2009/0152598 A1 | 6/2009 | Baek et al. |
| 2009/0191616 A1 | 7/2009 | Lu et al. |
| 2009/0198118 A1 | 8/2009 | Hayter et al. |
| 2009/0218239 A1 | 9/2009 | Gooding et al. |
| 2009/0259118 A1 | 10/2009 | Feldman et al. |
| 2009/0294306 A1 | 12/2009 | Feldman et al. |
| 2010/0006451 A1 | 1/2010 | Gordon et al. |
| 2010/0021637 A1 | 1/2010 | Revol et al. |
| 2010/0025238 A1 | 2/2010 | Gottlieb et al. |
| 2010/0030045 A1 | 2/2010 | Gottlieb et al. |
| 2010/0049021 A1 | 2/2010 | Jina et al. |
| 2010/0052892 A1 | 3/2010 | Allen et al. |
| 2010/0052897 A1 | 3/2010 | Allen et al. |
| 2010/0052898 A1 | 3/2010 | Allen et al. |
| 2010/0052915 A1 | 3/2010 | Allen et al. |
| 2010/0056873 A1 | 3/2010 | Allen et al. |
| 2010/0137779 A1 | 6/2010 | Seitz |
| 2010/0200538 A1 | 8/2010 | Petisce et al. |
| 2010/0279377 A1 | 11/2010 | Shah et al. |
| 2010/0286803 A1 | 11/2010 | Tillotson et al. |
| 2011/0027127 A1 | 2/2011 | Simpson et al. |
| 2011/0077490 A1 | 3/2011 | Simpson et al. |
| 2011/0105871 A1 | 5/2011 | Zimmermann et al. |
| 2011/0140703 A1 | 6/2011 | Chiao et al. |
| 2011/0224515 A1 | 9/2011 | Mir et al. |
| 2011/0230736 A1 | 9/2011 | Tepper et al. |
| 2011/0237925 A1 | 9/2011 | Yue et al. |
| 2011/0247934 A1 | 10/2011 | Wang et al. |
| 2011/0275918 A1 | 11/2011 | Yamashita et al. |
| 2011/0306853 A1 | 12/2011 | Black et al. |
| 2011/0319787 A1 | 12/2011 | Lamoise et al. |
| 2012/0018302 A1 | 1/2012 | Shiraki et al. |
| 2012/0037515 A1 | 2/2012 | Solanki |
| 2012/0067734 A1 | 3/2012 | Wang et al. |
| 2012/0078071 A1 | 3/2012 | Bohm et al. |
| 2012/0123232 A1 | 5/2012 | Najarian et al. |
| 2012/0172692 A1 | 7/2012 | Tamada et al. |
| 2012/0209244 A1 | 8/2012 | Gray |
| 2012/0277629 A1 | 11/2012 | Bernstein et al. |
| 2012/0323097 A9 | 12/2012 | Chowdhury |
| 2013/0053660 A1 | 2/2013 | Shieh |
| 2013/0065257 A1 | 3/2013 | Wang et al. |
| 2013/0135158 A1 | 5/2013 | Faraone et al. |
| 2013/0144131 A1 | 6/2013 | Wang et al. |
| 2013/0158376 A1 | 6/2013 | Hayter et al. |
| 2013/0225956 A1 | 8/2013 | Huang et al. |
| 2013/0281808 A1 | 10/2013 | Shieh |
| 2013/0338746 A1 | 12/2013 | Guvanasen et al. |
| 2013/0345597 A1 | 12/2013 | Hagino et al. |
| 2014/0135679 A1 | 5/2014 | Mann et al. |
| 2014/0259652 A1 | 9/2014 | Pushpala et al. |
| 2014/0275897 A1 | 9/2014 | Pushpala et al. |
| 2014/0275899 A1 | 9/2014 | Gottlieb et al. |

(56) References Cited

U.S. PATENT DOCUMENTS

| | | |
|---|---|---|
| 2014/0275907 A1 | 9/2014 | Feldman et al. |
| 2014/0303471 A1* | 10/2014 | Rajaraman .............. A61B 5/24 607/148 |
| 2014/0336487 A1 | 11/2014 | Wang et al. |
| 2014/0378804 A1 | 12/2014 | Kalvesten et al. |
| 2015/0073238 A1 | 3/2015 | Matsumoto et al. |
| 2015/0126834 A1 | 5/2015 | Wang et al. |
| 2015/0208970 A1 | 7/2015 | Huang |
| 2015/0243851 A1 | 8/2015 | Lee et al. |
| 2015/0276758 A1 | 10/2015 | Addisu |
| 2015/0313527 A1 | 11/2015 | Renlund |
| 2016/0029937 A1 | 2/2016 | Sia et al. |
| 2016/0058342 A1* | 3/2016 | Maiz-Aguinaga .......... A61B 5/14514 600/345 |
| 2016/0095541 A1 | 4/2016 | Wang et al. |
| 2016/0095547 A1 | 4/2016 | Wang et al. |
| 2016/0139069 A1 | 5/2016 | Wang |
| 2016/0157764 A1* | 6/2016 | Di Palma .............. C12Q 1/004 600/347 |
| 2016/0158514 A1 | 6/2016 | Stoeber et al. |
| 2016/0166184 A1 | 6/2016 | Teng et al. |
| 2016/0258945 A1 | 9/2016 | Malima et al. |
| 2016/0270704 A1 | 9/2016 | Deturk |
| 2016/0296149 A1 | 10/2016 | Polsky et al. |
| 2016/0302687 A1 | 10/2016 | Lee et al. |
| 2016/0370377 A1 | 12/2016 | Ahmad |
| 2017/0003766 A1 | 1/2017 | Budiman |
| 2017/0007813 A1 | 1/2017 | Negi et al. |
| 2017/0035331 A1 | 2/2017 | Parajape et al. |
| 2017/0127989 A1 | 5/2017 | Feldman et al. |
| 2017/0128009 A1 | 5/2017 | Pushpala et al. |
| 2017/0164881 A1 | 6/2017 | Fujita et al. |
| 2017/0251959 A1 | 9/2017 | Feldman et al. |
| 2017/0251960 A1 | 9/2017 | Crouther et al. |
| 2017/0347925 A1 | 12/2017 | Wang et al. |
| 2018/0116572 A1 | 5/2018 | Simpson et al. |
| 2018/0140235 A1 | 5/2018 | Pushpala et al. |
| 2018/0279929 A1* | 10/2018 | Huang ............ A61B 5/150022 |
| 2018/0317820 A1 | 11/2018 | Pace et al. |
| 2018/0338712 A1* | 11/2018 | Cass .................. A61B 5/14514 |
| 2019/0008425 A1 | 1/2019 | Srinivasan et al. |
| 2019/0022365 A1 | 1/2019 | Chowdhury et al. |
| 2019/0029577 A1 | 1/2019 | Koelker et al. |
| 2019/0090811 A1 | 3/2019 | Reitz et al. |
| 2019/0091455 A1 | 3/2019 | Reitz et al. |
| 2019/0094169 A1 | 3/2019 | Shah et al. |
| 2019/0110724 A1 | 4/2019 | Kamath et al. |
| 2019/0125223 A1 | 5/2019 | Wang et al. |
| 2019/0167167 A1 | 6/2019 | Mitchell et al. |
| 2019/0209095 A1 | 7/2019 | Kamath et al. |
| 2019/0223795 A1 | 7/2019 | Patolsky et al. |
| 2019/0224712 A1 | 7/2019 | Petisce et al. |
| 2019/0241926 A1 | 8/2019 | Mckinlay et al. |
| 2019/0261907 A1 | 8/2019 | Brister et al. |
| 2019/0274599 A1 | 9/2019 | Polsky et al. |
| 2019/0274600 A1 | 9/2019 | Pesantez et al. |
| 2019/0298210 A1 | 10/2019 | Bennet et al. |
| 2019/0307379 A1 | 10/2019 | Boock et al. |
| 2019/0309433 A1 | 10/2019 | Sattayasamitsathit et al. |
| 2019/0310219 A1 | 10/2019 | Boock |
| 2019/0357827 A1 | 11/2019 | Li et al. |
| 2020/0029876 A1 | 1/2020 | Brister et al. |
| 2020/0037938 A1 | 2/2020 | Rong et al. |
| 2020/0101286 A1 | 4/2020 | Windmiller et al. |
| 2020/0121902 A1 | 4/2020 | Pushpala et al. |
| 2020/0178853 A1 | 6/2020 | Pushpala et al. |
| 2020/0187778 A1 | 6/2020 | Brister et al. |
| 2020/0214566 A1 | 7/2020 | Allen et al. |
| 2020/0254240 A1 | 8/2020 | Windmiller et al. |
| 2020/0297997 A1 | 9/2020 | Windmiller et al. |
| 2020/0305771 A1 | 10/2020 | Feldman et al. |
| 2020/0359949 A1 | 11/2020 | Brauker et al. |
| 2020/0405234 A1 | 12/2020 | Pushpala et al. |
| 2021/0045663 A1 | 2/2021 | Simpson et al. |
| 2021/0045665 A1 | 2/2021 | Simpson et al. |
| 2021/0045666 A1 | 2/2021 | Simpson et al. |
| 2021/0100452 A1 | 4/2021 | Brister et al. |
| 2021/0100504 A1 | 4/2021 | Pushpala et al. |
| 2021/0100505 A1 | 4/2021 | Pushpala et al. |
| 2021/0183508 A1 | 6/2021 | Parker et al. |
| 2021/0187286 A1 | 6/2021 | Windmiller et al. |
| 2021/0190719 A1 | 6/2021 | LaTour et al. |
| 2021/0345916 A1 | 11/2021 | Boock et al. |
| 2021/0353229 A1 | 11/2021 | Pierart et al. |
| 2021/0379370 A1 | 12/2021 | Windmiller et al. |
| 2021/0386338 A1 | 12/2021 | Zhang et al. |
| 2021/0393201 A1 | 12/2021 | Morelock et al. |
| 2022/0031244 A1 | 2/2022 | Windmiller et al. |
| 2022/0047190 A1 | 2/2022 | Taylor et al. |
| 2022/0054813 A1 | 2/2022 | Pushpala et al. |
| 2022/0054814 A1 | 2/2022 | Pushpala et al. |
| 2022/0104773 A1 | 4/2022 | Lee et al. |
| 2022/0151516 A1 | 5/2022 | Wang et al. |
| 2022/0151518 A1 | 5/2022 | Pushpala et al. |
| 2022/0151519 A1 | 5/2022 | Pushpala et al. |
| 2022/0151558 A1 | 5/2022 | Pushpala et al. |
| 2022/0175278 A1 | 6/2022 | Campbell et al. |
| 2022/0175279 A1 | 6/2022 | Pushpala et al. |
| 2022/0175282 A1 | 6/2022 | Hoss et al. |
| 2022/0214300 A1 | 7/2022 | Wang et al. |
| 2022/0225901 A1 | 7/2022 | Chapman et al. |
| 2022/0233107 A1 | 7/2022 | Pushpala et al. |
| 2022/0249189 A1 | 8/2022 | Choi et al. |
| 2022/0298291 A1 | 9/2022 | Shin et al. |
| 2022/0322975 A1 | 10/2022 | Baker et al. |
| 2022/0322977 A1 | 10/2022 | Simpson et al. |
| 2022/0370011 A1 | 11/2022 | Windmiller et al. |
| 2023/0074798 A1 | 3/2023 | Tangney et al. |
| 2023/0094419 A1 | 3/2023 | Mansfield, III et al. |
| 2023/0099617 A1 | 3/2023 | Mansfield, III et al. |
| 2023/0137258 A1 | 5/2023 | Windmiller |
| 2023/0190147 A1 | 6/2023 | Campbell et al. |

FOREIGN PATENT DOCUMENTS

| | | |
|---|---|---|
| EP | 1006868 B1 | 6/2004 |
| EP | 1 372 602 B1 | 4/2007 |
| EP | 1792565 B1 | 10/2008 |
| EP | 1 187 653 B1 | 3/2010 |
| EP | 2 898 821 B1 | 12/2017 |
| EP | 3 381 370 A1 | 10/2018 |
| JP | H-02-031741 A | 2/1990 |
| JP | H-07-275227 A | 10/1995 |
| JP | 2003-038464 A | 2/2003 |
| JP | 2003-038465 A | 2/2003 |
| JP | 2005-087613 A | 4/2005 |
| JP | 2006-510467 A | 4/2005 |
| JP | 2005-525141 A | 8/2005 |
| JP | 2005-322591 A | 11/2005 |
| JP | 2008-512162 A | 4/2008 |
| JP | 2008-540013 A | 11/2008 |
| KR | 10-2016-0108111 A | 9/2016 |
| WO | WO-00/74763 A2 | 12/2000 |
| WO | WO-00/74763 A3 | 12/2000 |
| WO | WO-2006/060106 A1 | 6/2006 |
| WO | WO-2006/093422 A1 | 9/2006 |
| WO | WO-2006/116242 A2 | 11/2006 |
| WO | WO-2006/116242 A3 | 11/2006 |
| WO | WO-2007/040938 A1 | 4/2007 |
| WO | WO-2009/034313 A2 | 3/2009 |
| WO | WO-2009/034313 A3 | 3/2009 |
| WO | WO-2009/064164 A2 | 5/2009 |
| WO | WO-2009/064164 A3 | 5/2009 |
| WO | WO-2009/124095 A1 | 10/2009 |
| WO | WO-2010/014959 A2 | 2/2010 |
| WO | WO-2010/014959 A3 | 2/2010 |
| WO | WO-2010/022252 A2 | 2/2010 |
| WO | WO-2010/022252 A3 | 2/2010 |
| WO | WO-2010/045247 A1 | 4/2010 |
| WO | WO-2010/059276 A1 | 5/2010 |
| WO | WO-2010/120364 A2 | 10/2010 |
| WO | WO-2010/120364 A3 | 10/2010 |
| WO | WO-2011/056095 A1 | 5/2011 |

(56) References Cited

FOREIGN PATENT DOCUMENTS

| WO | WO-2012/020332 A2 | 2/2012 |
|----|----|----|
| WO | WO-2012/020332 A3 | 2/2012 |
| WO | WO-2012/142625 A2 | 10/2012 |
| WO | WO-2012/142625 A3 | 10/2012 |
| WO | WO-2013/058879 A2 | 4/2013 |
| WO | WO-2013/058879 A3 | 4/2013 |
| WO | WO-2014120114 A1 | 8/2014 |
| WO | WO-2015/073459 A1 | 5/2015 |
| WO | WO-2016189301 A1 | 12/2016 |
| WO | WO-2017/129980 A1 | 8/2017 |
| WO | WO-2017/189707 A1 | 11/2017 |
| WO | WO-2018/017196 A1 | 1/2018 |
| WO | WO-2018/071265 A1 | 4/2018 |
| WO | WO-2018/164886 A1 | 9/2018 |
| WO | WO-2018/170363 A1 | 9/2018 |
| WO | WO-2019/156934 A1 | 8/2019 |
| WO | WO-2019/222615 A1 | 11/2019 |
| WO | WO-2019/239258 A1 | 12/2019 |
| WO | WO-2020/023804 A1 | 1/2020 |
| WO | WO-2021/015389 A1 | 1/2021 |
| WO | WO-2021/025260 A1 | 2/2021 |
| WO | WO-2021/086690 A1 | 5/2021 |
| WO | WO-2021118124 A1 | 6/2021 |
| WO | WO-2021118431 A1 | 6/2021 |
| WO | WO-2022/026764 A1 | 2/2022 |
| WO | WO-2022066985 A1 | 3/2022 |
| WO | WO-2022066992 A1 | 3/2022 |
| WO | WO-2022090741 A1 | 5/2022 |
| WO | WO-2022136785 A1 | 6/2022 |
| WO | WO-2023055755 A1 | 4/2023 |
| WO | WO-2023064877 A1 | 4/2023 |
| WO | WO-2023133468 A1 | 7/2023 |

OTHER PUBLICATIONS

American Diabetes Association® Press Release (2020). "American Diabetes Association® Applauds policymakers' Focus on Addressing High Costs of Insulin for Seven Million Americans," 4 pages.
Bantle, J.P. et al. (1997). "Glucose measurement in patients with diabetes mellitus with dermal interstitial fluid," J. Lab. Clin. Med. 130:436-441.
Beckles, G.L. et al. (2016). "Disparities in the prevalence of diagnosed diabetes—United States, 1999-2002 and 2011-2014," MMWR 65:1265-1269.
Cao, J. et al. (2017). "Validation of capillary blood analysis and capillary testing mode on the epoc Point of Care system," Pract. Lab. Med. 9:24-27.
Castle, J.R. et al. (2012). "The accuracy benefit of multiple amperometric glucose sensors in people with type 1 diabetes," Diabetes Care 35:706-710.
Chang, H. et al. (2017). "A swellable microneedle patch to rapidly extract skin interstitial fluid for timely metabolic analysis," Adv. Mater. 29:1702243.
Dexcom (2020). Analyst Day Presentation, 27 total pages.
Dexcom (2020). Analyst Day Presentation, 19 total pages.
Diabetes Care (2021). "7. Diabetes Technology: Standards of Medical Care in Diabetes—2021," Diabetes Care 44(Supplement 1):S85-S99.
Donnelly, R.F. et al. (2007). "Microstructured Devices for Transdermal Drug Delivery and Minimally-Invasive Patient Monitoring," Recent Patents on Drug Delivery & Formulation 1:195-200.
Extended European Search Report dated May 8, 2015, for EP Application No. 12 842 020.5, filed on Aug. 31, 2012, 7 pages.
Extended European Search Report dated Oct. 27, 2022, for EP Application No. 21 850 331.6, filed on Jul. 29, 2021, 8 pages.
Fang, M. et al. (2021). "Trends in Diabetes Treatment and Control in U.S. Adults, 1999-2018," N. Engl. Med. 384:2219-2228.
Final Office Action dated Aug. 19, 2016, for U.S. Appl. No. 14/965,755, filed Dec. 10, 2015, 17 pages.
Final Office Action dated Nov. 28, 2016, for U.S. Appl. No. 14/342,536, filed Jul. 30, 2014, 34 pages.
Final Office Action dated May 18, 2018, for U.S. Appl. No. 15/687,145, filed Aug. 25, 2017, 23 pages.
Final Office Action dated Dec. 7, 2020, for U.S. Appl. No. 15/961,793, filed Apr. 24, 2018, 13 pages.
Final Office Action dated May 21, 2021, for U.S. Appl. No. 16/051,398, filed Jul. 31, 2018, 11 pages.
Final Office Action dated Jun. 9, 2021, for U.S. Appl. No. 16/169,939, filed Oct. 24, 2018, 24 pages.
Final Office Action dated Sep. 23, 2021, for U.S. Appl. No. 15/913,709, filed Mar. 6, 2018, 17 pages.
Final Office Action dated May 9, 2022, for U.S. Appl. No. 17/389,153, filed Jul. 29, 2021, 17 pages.
Final Office Action dated Aug. 15, 2022, for U.S. Appl. No. 16/051,398, filed Jul. 31, 2018, 15 pages.
Final Office Action dated Oct. 27, 2022, for U.S. Appl. No. 15/913,709, filed Mar. 6, 2018, 21 pages.
French, D.P. et al. (2008). "Original Article: Psychological Care Self-monitoring of blood glucose changed non-insulin-treated Type 2 diabetes patients' beliefs about diabetes and self-monitoring in a randomized trial," Diav. Med. 25:1218-1228.
Gittard, S.D. et al. (2009). "Fabrication of Polymer Microneedles Using a Two-Photon Polymerization and Micromolding Process," J. Diabetes Sci. Technol. 3:304-311.
Grady, M. et al. (2017). "Examining the Impact of a Novel Blood Glucose Monitor With Color Range Indicator on Decision-Making in Patients With Type 1 and Type 2 Diabetes and its Association With Patient Numeracy Level," JMIR Diabetes 2:e24.
Grady, M. et al. (2018). "Use of Blood Glucose Meters Featuring Color Range Indicators Improves Glycemic Control in Patients with Diabetes in Comparison to Blood Glucose Meters Without Color (ACCENTS Study)," J. Diab. Sci. Tech. 12:1211-1219.
Groenendaal, W. et al. (2008). "Modeling Glucose and Water Dynamics in Human Skin," Diab. Tech. Therap. 10:283-293.
International Search Report dated Dec. 30, 2021, for PCT Application No. PCT/US2021/043786, filed on Jul. 29, 2021, 7 pages.
International Search Report dated Sep. 10, 2020, for PCT Application No. PCT/US2020/037379, filed on Jun. 12, 2020, 2 pages.
International Search Report dated Feb. 4, 2021, for PCT Application No. PCT/US2020/056517, filed on Oct. 20, 2020, 2 pages.
International Search Report dated Sep. 30, 2021, for PCT Application No. PCT/US2021/040385, filed on Jul. 2, 2021, 2 pages.
International Search Report dated Aug. 29, 2022, for PCT Application No. PCT/US2022/028196, filed on May 6, 2022, 2 pages.
International Search Report dated Jun. 27, 2013, for PCT Application No. PCT/US2012/053544, filed on Aug. 31, 2012, 4 pages.
Jeon, G. et al. (2011). "Electrically Actuatable Smart Nanoporous Membrane for Pulsatile Drug Release," Nano Lett. 11:1284-1288.
Jina, A et al. (2014). "Design, development, and evaluation of a novel microneedle array-based continuous glucose monitor," J. Diabetes Sci. Technol. 8:483-487.
Juvenile Diabetes Research Foundation Continuous Glucose Monitoring Study Group (2008). "Continuous Glucose Monitoring and Intensive Treatment of Type 1 Diabetes," N. Engl. Med. 359:1464-1476.
Karter, A.J. et al. (2021). "Association of Real-time Continuous Glucose Monitoring with Glycemic Control and Acute Metabolic Events Among Patients with Insulin-Treated Diabetes," JAMA 325:2273-2284.
Lhernould, M.S. et al. (2015). "Review of Patents for Microneedle Application Devices Allowing Fluid Injections Through the Skin," Recent Patents on Drug Delivery & Formulation 9:146-157.
Malitesta et al. (1990). "Glucose fast-response amperometric sensor based on glucose oxidase immobilized in an electropolymerized poly(o-phenylenediamine) film," Anal. Chem. 62:2735-2740.
Martens, T. et al. (2021). "Effect of Continuous Glucose Monitoring on Glycemic Control in Patients with Type 2 Diabetes Treated with Basal Insulin a Randomized Clinical Trial," JAMA 325:2262-2272.
Mcclatchey, P.M. et al. (2019). "Fibrotic Encapsulation Is the Dominant Source of Continuous Glucose Monitor Delays," Diabetes 68:1892-1901.
Miller, P.R. et al. (2011). "Integrated carbon fiber electrodes within hollow polymer microneedles for transdermal electrochemical sensing," BioMicrofluidics 5(1):013415.

(56) References Cited

OTHER PUBLICATIONS

Mohan, A.M. (2017). "Continuous minimally-invasive alcohol monitoring using microneedle sensor arrays," Biosensors and Bioelectronics 91:574-579.
Neerken, S. et al. (2004). "Characterization of age-related effects in human skin: A comparative study that applies confocal laser scanning microscopy and optical coherence tomography," J. Biomed. Optics 9:274-281.
Non-Final Office Action dated Mar. 10, 2016, for U.S. Appl. No. 14/965,755, filed Dec. 10, 2015, 15 pages.
Non-Final Office Action dated Mar. 30, 2016, for U.S. Appl. No. 14/342,536, filed Jul. 30, 2014, 31 pages.
Non-Final Office Action dated Mar. 9, 2017, for U.S. Appl. No. 14/965,755, filed Dec. 10, 2015, 17 pages.
Non-Final Office Action dated Apr. 6, 2017, for U.S. Appl. No. 14/342,536, filed Jul. 30, 2014, 32 pages.
Non-Final Office Action dated Nov. 1, 2017, for U.S. Appl. No. 15/687,145, filed Aug. 25, 2017, 19 pages.
Non-Final Office Action dated Jan. 19, 2018, for U.S. Appl. No. 14/843,926, filed Sep. 2, 2015, 11 pages.
Non-Final Office Action dated Apr. 13, 2020, for U.S. Appl. No. 15/961,793, filed Apr. 24, 2018, 13 pages.
Non-Final Office Action dated Sep. 3, 2020, for U.S. Appl. No. 16/169,939, filed Oct. 24, 2018, 19 pages.
Non-Final Office Action dated Sep. 16, 2020, for U.S. Appl. No. 15/913,709, filed Mar. 6, 2018, 15 pages.
Non-Final Office Action dated Oct. 16, 2020, for U.S. Appl. No. 16/051,398, filed Jul. 31, 2018, 13 pages.
Non-Final Office Action dated Nov. 4, 2021, for U.S. Appl. No. 16/169,939, filed Oct. 24, 2018, 20 pages.
Non-Final Office Action dated Nov. 26, 2021, for U.S. Appl. No. 16/051,398, filed Jul. 31, 2018, 15 pages.
Non-Final Office Action dated Nov. 29, 2021, for U.S. Appl. No. 17/389,153, filed Jul. 29, 2021, 14 pages.
Non-Final Office Action dated Apr. 8, 2022, for U.S. Appl. No. 17/650,056, filed Feb. 4, 2022, 14 pages.
Non-Final Office Action dated May 13, 2022, for U.S. Appl. No. 15/913,709, filed Mar. 6, 2018, 20 pages.
Non-Final Office Action dated Dec. 21, 2022, for U.S. Appl. No. 16/051,398, filed Jul. 31, 2018, 12 pages.
Non-Final Office Action dated Jan. 27, 2023, for U.S. Appl. No. 17/971,415, filed Oct. 21, 2022, 15 pages.
Non-Final Office Action dated Feb. 16, 2023, for U.S. Appl. No. 17/738,990, filed May 6, 2022, 8 pages.
Notice of Allowance dated Jul. 6, 2017, for U.S. Appl. No. 14/965,755, filed Dec. 10, 2015, 12 pages.
Notice of Allowance dated Jul. 12, 2017, for U.S. Appl. No. 14/342,536, filed Jul. 30, 2014, 14 pages.
Notice of Allowance dated Feb. 13, 2018, for U.S. Appl. No. 14/843,926, filed Sep. 2, 2015, 8 pages.
Notice of Allowance dated Aug. 24, 2018, for U.S. Appl. No. 15/687,145, filed Aug. 25, 2017, 7 pages.
Notice of Allowance dated May 25, 2021, for U.S. Appl. No. 15/961,793, filed Apr. 24, 2018, 11 pages.
Notice of Allowance dated Sep. 12, 2022, for U.S. Appl. No. 17/389,153, filed Jul. 29, 2021, 8 pages.
Polonsky, W.H. et al. (2011). "A survey of blood glucose monitoring in patients with type 2 diabetes: Are recommendations from health care professionals being followed?" Curr. Med. Res. & Opinion 27:31-37.
Rigla, M. et al. (2018). "Human Subcutaneous Tissue Response to Glucose Sensors: Macrophages Accumulation Impact on Sensor Accuracy," Diabetes Technology & Therapeutics 20:296-302.
Sachdeva, V. et al. (2011). "Microneedles and their applications," Recent Patents on Drug Delivery & Formulation 5:95-132.
Sheikh, Z. et al. (2015). "Macrophages, Foreign Body Giant Cells and Their Response to Implantable Biomaterials," Materials 8:5671-5701.
Shi, T. et al. (2016). "Modeling and Measurement of Correlation between Blood and Interstitial Glucose Changes," J. Diab. Res. vol. 2016, 9 pages.
Singh, T.R.R. et al. (2010). "Microporation techniques for enhanced delivery of therapeutic agents," Recent Patents on Drug Delivery & Formulation 4:1-17.
Swedish Search Report dated Feb. 3, 2023 for SE Application No. 2350067-1, 7 pages.
Texas Instruments (Sep. 2007). Data sheet for a LMP2234 quad micropower, 1.6V, precision, operational amplifier with CMOS input, Sep. 2007, revised Mar. 2013, 31 total pages.
Windmiller, J.R. (2012). "Molecular scale biocomputing: An enzyme logic approach," University of California, San Diego, A dissertation submitted in partial satisfaction of the requirements for the degree Doctor of Philosophy in Electrical Engineering (Photonics), 78 total pages.
Windmiller, J.R. et al. (2011). "Bicomponent microneedle array biosensor for minimally-invasive glutamate monitoring," Electroanalysis 23:2302-2309.
Windmiller, J.R. et al. (2011). "Microneedle array-based carbon paste amperometric sensors and biosensors," Analyst 136:1846-1851.
Written Opinion of the International Searching Authority dated Dec. 30, 2021, for PCT Application No. PCT/US2021/043786, filed on Jul. 29, 2021, 10 pages.
Written Opinion of the International Searching Authority dated Sep. 10, 2020, for PCT Application No. PCT/US2020/037379, filed on Jun. 12, 2020, 4 pages.
Written Opinion of the International Searching Authority dated Feb. 4, 2021, for PCT Application No. PCT/US2020/056517, filed on Oct. 20, 2020, 5 pages.
Written Opinion of the International Searching Authority dated Sep. 30, 2021, for PCT Application No. PCT/US2021/040385, filed on Jul. 2, 2021, 2 pages.
Written Opinion of the International Searching Authority dated Aug. 29, 2022, for PCT Application No. PCT/US2022/028196, filed on May 6, 2022, 5 pages.
Written Opinion of the International Searching Authority dated Jun. 27, 2013, for PCT Application No. PCT/US2012/053544, filed on Aug. 31, 2012, 15 pages.
Yoon, Y. et al. (2013). "Fabrication of a Microneedle/CNT Hierarchical Micro/Nano Surface Electrochemical Sensor and Its In-Vitro Glucose Sensing Characterization," Sensors 13:16672-16681.
Al Hayek et al., "Patient Satisfaction and Clinical Efficacy of Novel Blood Glucose Meters Featuring Color Range Indicators in Patients With Type 2 Diabetes: A Prospective Study" Cureus Oct. 27, 2020; 12(10):e11195. doi: 10.7759/cureus.11195.
Allen et al., "Continuous glucose monitoring counseling improves physical activity behaviors of individuals with type 2 diabetes: A randomized clinical trial" Diabetes Res Clin Pract. Jun. 2008; 80(3): 371-379. doi:10.1016/j.diabres.2008.01.006.
Barrett et al., "Risk for Newly Diagnosed Diabetes 30 Days After SARS-COV-2 Infection Among Persons Aged 18 Years—United States, Mar. 1, 2020-Jun. 28, 2021" MMWR Morb Mortal Wkly Rep. Jan. 14, 2022; 71(2):59-65. doi: 10.15585/mmwr.mm7102e2.
Brown, C., "Design of Electronics for Wearable Electrochemical Sensors", University of California, San Diego, 2019, 39 pgs.
Centers for Disease Control, "National Diabetes Statistics Report 2020 Estimates of Diabetes and Its Burden in the United States" (2020) 32 pages.
Dunkin et al., "Scarring occurs at a critical depth of skin injury: precise measurement in a graduated dermal scratch in human volunteers" Plast Reconstr Surg. May 2007; 119(6):1722-1732. doi: 10.1097/01.prs.0000258829.07399.f0.
Ehrhardt et al, "Behavior Modification in Prediabetes and Diabetes: Potential Use of Real-Time Continuous Glucose Monitoring" Journal of Diabetes Science and Technology Mar. 2019; 13(2):271-275.
Ehrhardt et al., "Continuous Glucose Monitoring As a Behavior Modification Tool" Clin Diabetes. Apr. 2020; 38(2):126-131. doi: 10.2337/cd19-0037.

(56) References Cited

OTHER PUBLICATIONS

Ehrhardt et al, "The Effect of Real-Time Continuous Glucose Monitoring on Glycemic Control in Patients with Type 2 Diabetes Mellitus" Journal of Diabetes Science and Technology May 2011; 5(3):668-675.
Extended European Search Report dated Mar. 30, 2023, for European Application No. EP20881425.1, 8 pages.
Fonda et al., "The Cost-Effectiveness of Real-Time Continuous Glucose Monitoring (RT-CGM) in Type 2 Diabetes" Journal of Diabetes Science and Technology (2016) 10(4):898-904.
Han et al., "The End of the Road for the YSI 2300 Analyzer: Where Do We Go Now?" Journal of Diabetes Science and Technology (2020) 14(3):595-600.
Han et al., "The YSI 2300 Analyzer Replacement Meeting Report" Journal of Diabetes Science and Technology (2020) 14(3):679-686.
Non-Final Office Action dated Mar. 9, 2023 for U.S. Appl. No. 17/389,156, filed Jul. 29, 2021, 24 pages.
Non-Final Office Action dated May 2, 2023 for U.S. Appl. No. 15/913,709, filed Mar. 6, 2018, 18 pages.
Non-Final Office Action dated May 24, 2023 for U.S. Appl. No. 18/086,543, filed Dec. 21, 2022, 19 pages.
Non-Final Office Action dated Jun. 2, 2023, for U.S. Appl. No. 17/367,274, filed Jul. 2, 2021, 27 pages.
Non-Final Office Action dated Jun. 20, 2023, for U.S. Appl. No. 17/073,331, filed Oct. 17, 2020, 10 pages.
Notice of Allowance dated Jun. 12, 2023, for U.S. Appl. No. 17/971,415, filed Oct. 21, 2022, 14 pages.
Notice of Allowance dated Jun. 12, 2023, for U.S. Appl. No. 17/738,990, filed May 6, 2022, 7 pages.
Sharifi et al., "Redundancy in Glucose Sensing: Enhanced Accuracy and Reliability of an Electrochemical Redundant Sensor for Continuous Glucose Monitoring" Journal of Diabetes Science and Technology (2016) 10(3):669-678.
Turner et al., "Intensive blood-glucose control with sulphonylureas or insulin compared with conventional treatment and risk of complications in patients with type 2 diabetes (UKPDS 33)" The Lancet Sep. 1998; 352(9131):837-853.
Vigersky et al., "Short- and Long-Term Effects of Real-Time Continuous Glucose Monitoring in Patients with Type 2 Diabetes" Diabetes Care Jan. 2012; 35:32-38.
Wolicki et al., "Epidemiology and Prevention of Vaccine-Preventable Diseases: Chapter 6: Vaccine Administration" Centers for Disease Control and Prevention (2021) 17 pages.
World Health Organization, "Diabetes", Sep. 16, 2022, 5 pages.
Young et al., "Glucose Self-monitoring in Non-Insulin-Treated Patients With Type 2 Diabetes in Primary Care Settings: A Randomized Trial" JAMA Intern Med. Jul. 2017; 177(7):920-929.

* cited by examiner

HETEROGENEOUS INTEGRATION OF SILICON-FABRICATED SOLID MICRONEEDLE SENSORS AND CMOS CIRCUITRY

CROSS REFERENCES TO RELATED APPLICATIONS

The Present Application is a continuation application of U.S. patent application Ser. No. 15/961,793, filed on Apr. 24, 2018, which claims priority to U.S. Provisional Patent Application No. 62/492,142, filed on Apr. 29, 2017, each of which is hereby incorporated by reference in its entirety.

STATEMENT REGARDING FEDERALLY SPONSORED RESEARCH OR DEVELOPMENT

Not Applicable

BACKGROUND OF THE INVENTION

Field of the Invention

The present invention generally relates to sensors.

Description of the Related Art

The integration of silicon-fabricated microneedles with conventional silicon complementary metal-oxide semiconductor ("CMOS") circuitry is of utmost importance in perpetuating the miniaturization efforts of body-worn medical devices. Despite the current state of semiconductor miniaturization and packaging, the creation of a heterogeneous system comprised of microneedle-based sensors and the CMOS circuitry required to transduce the signals generated by such devices has posed a formidable challenge to those aiming to create low-profile, highly-integrated body-worn sensors for the quantification of physiological or biochemical signals. Indeed, leveraging state-of-the-art semiconductor processing and packaging methods in conjunction with CMOS-based circuitry and recent developments in minimally-invasive silicon-based microneedle devices for physiological and biochemical sensing would enable the construction of a self-contained sensing system in a single package.

U.S. Pat. No. 8,506,529 for a Method and structure of monolithetically integrated microneedle biochip discloses a method and device using CMOS and MEMS fabrication techniques for making an integrated microneedle device with integrated circuits. Merely by way of example, the technology can be applied to bio and chemical sensing, and other bioMEMS applications. In some embodiments, the integrated circuits are completed using standard IC processes. For example, an array of microneedles are fabricated on top of the IC substrate followed by formation of micro fluidic channels in the substrate. On-chip integrated circuits enable real-time sensing and intelligent drug delivery.

U.S. Pat. No. 5,953,306 for a Micro needle probe apparatus having probes cantilevered over respective electronic circuits, moving medium memory device including same and method of making same discloses micro needle probe apparatus that includes a probe and its associated electronic circuit. The electronic circuit is formed in a substrate and includes at least one metal interconnection layer. The probe is cantilevered over the electronic circuit and is composed of a metal probe arm, a support post that anchors one end of the probe arm to the substrate, and a micro needle mounted adjacent the moveable end of the probe arm. The probe apparatus may be used as the read/write mechanism of the moving-medium type memory device.

U.S. Pat. No. 8,452,369 for a CMOS compatible microneedle structures discloses an electronic device for sensing and/or actuating, the electronic device comprising at least one microneedle (10) on a substrate (1), each of the microneedles (10) comprising at least one channel (7, 8) surrounded by an insulating layer (6).

Prior art solutions have been concerned with the integration of silicon-based microneedle arrays and CMOS circuitry as discrete devices populating a printed circuit board; in certain circumstances, these metallic wires are coated with a layer of metal salt, such as a silver wire functionalized on the surface with a layer of silver chloride. Such integration fails to minimize device footprint, especially in x-y dimensions, since device area constitutes the summation of the area of any discrete CMOS circuitry, microneedle sensor (s), and area devoted to interconnect between these two entities on said printed circuit board. Under such a design philosophy, efforts have largely been devoted to ultra-large scale integration of CMOS circuitry and the creation of CMOS systems-on-a-chip to minimize the number of discrete CMOS devices populating a sensing system. Likewise, recent efforts have been directed at reducing the number of components required to realize microneedle-mediated sensing via the integration of electrophysiological and electrochemical sensors on self-contained solid microneedle devices, thereby obviating the need for separate hollow microneedle-based lumens for physiological fluid extraction and an adjoining chamber for which the chemical reaction and/or electrochemical detection are intended to occur. The heterogeneous integration of CMOS- and microneedle-based capabilities into a single package would facilitate a novel means to the construction of self-contained sensor-transducer devices that require substantially less footprint than conventional discrete constituents that comprise current body-worn sensing systems can provide.

BRIEF SUMMARY OF THE INVENTION

The technology described herein relates to methods of integration and packaging of heterogenous semiconductor substrates.

One aspect of the present invention is a skin-adorned physiological or biochemical sensing system. The system comprises a first substrate and a second substrate. The first substrate features an anterior and a posterior surface. The first substrate comprises an array of solid microneedles on the anterior surface designed to penetrate a biological interface to access a physiological fluid or tissue. Each microneedle contains an addressable metal electrode located on the surface of the microneedle which is in electrical communication with a metal surface located on the posterior surface of the first substrate by means of a conductive conduit, to form a sensor component capable of electrical interface with the physiological fluid or tissue. The second substrate has an anterior and a posterior surface. The second substrate comprises integrated circuitry on the anterior surface designed to transduce at least one signal produced by an electrophysiological or electrochemical reaction occurring at the metal electrode, to form a transducer component. The posterior surface of the first substrate is stacked to the anterior surface of the second substrate. The first substrate is bonded to the second substrate to create an electrical interconnect between the first substrate and the second substrate. A sensing system is formed that is capable of interpreting the signal arising from the electrophysiological or electrochemical reaction to ascertain the level of some physiological or biochemical entity.

Yet another aspect of the present invention is a method for the heterogeneous and monolithic integration of a semiconductor-based solid microneedles sensor and a semiconductor-based CMOS circuitry transducer. The method includes bonding a plurality of pads located on the posterior surface of sensor to a plurality of pads on either the anterior or posterior surface of a transducer to facilitate electrical communication between a sensor and the transducer. The sensor comprises a plurality of solid microneedles on the anterior surface of a substrate, each of the plurality of microneedles comprising an addressable sensing electrode. The transducer comprises a potentiostat, an analog front end, an amplifier, a filter, an analog-to-digital converter, microcontroller, and a wireless radio; Each of the plurality of sensing electrodes is accessible on a posterior surface of the substrate by means of a plurality of vertically-oriented conducting channels, wherein at a location on the posterior surface in which each of plurality of vertically-oriented conducting channels exit from the substrate. A plurality of conductive pads are positioned to facilitate bonding to the surface of a second substrate.

Yet another aspect of the present invention is a method for the heterogeneous and monolithic integration of a semiconductor-based solid microneedles sensor and a semiconductor-based CMOS circuitry transducer. The method includes mating a first substrate to a second substrate such that a posterior surface of the first substrate is bonded to an anterior surface of the second substrate. The first substrate contains a transducer and the second substrate containing a sensor. The sensor comprises a plurality of solid microneedles on the anterior surface of a substrate. Each of the plurality of microneedles comprises an addressable sensing electrode. The transducer comprises a potentiostat, an analog front end, an amplifier, a filter, an analog-to-digital converter, microcontroller, and a wireless radio. Each of the plurality of sensing electrodes is accessible on a posterior surface of the substrate by means of a plurality of vertically-oriented conducting channels, wherein at a location on the posterior surface in which each of plurality of vertically-oriented conducting channels exit from the substrate. A plurality of conductive pads are positioned to facilitate bonding to the surface of a second substrate.

Having briefly described the present invention, the above and further objects, features and advantages thereof will be recognized by those skilled in the pertinent art from the following detailed description of the invention when taken in conjunction with the accompanying drawings.

DETAILED DESCRIPTION OF THE INVENTION

To facilitate increased patient compliance and improve the treatment of acute or chronic disease, body-adorned medical devices such as non-invasive sensor patches as well as minimally-invasive subcutaneously- and intracutaneously-implanted sensors have substantially expanded in use over the past decade. Much of this proliferation has been a result of advancements in electrochemical sensor technology, which enables the quantification of circulating analytes in physiological fluids (blood, interstitial fluid, etc.) in miniaturized and compact platforms. These platforms, which integrate the sensor and transducer constituents into a single device, have been applied to such embodiments as continuous glucose monitoring. Although the current state-of-the-art has resulted in the widespread utilization of body-worn devices in the healthcare domain, the realization of truly low-profile and potentially skin-conformal skin-adorned or skin-adhered medical devices remains elusive as current limitations with electronic device packaging often entails the mounting and interconnect, in a 2-dimensional fashion, of discrete components populating a printed circuit board.

The present invention is a method for the three-dimensional ("3D") packaging and interconnection of heterogeneous, semiconductor-based systems for body-worn health and wellness devices, such as MEMS-fabricated microneedle arrays and CMOS-based transducers. One aspect of the present invention is a novel method of die attaching via stacking and interconnection of CMOS- and MEMS-based dies as a means to achieve 2.5D or 3D integration. Another aspect of the present invention is a method of fabricating CMOS and MEMS systems on geographically distinct regions of a shared surface of substrate whereby said systems are interconnected to one another by means of conductive traces or through-silicon vias. Another aspect of the present invention is a method of fabricating CMOS and MEMS on opposing surfaces of a substrate whereby interconnect between the two systems is facilitated by through-silicon vias. The ability to perform MEMS-to- CMOS packaging via stacked wire-bonding, reflow soldering of solder balls, or stud-bumping in conjunction with silicon or epoxy interposers enables the construction of vertically-integrated 2.5- or 3-dimensional self-contained sensing systems. Likewise, co-substrate integration of microneedles and CMOS circuitry represents another compelling solution enabled by through-silicon vias (TSVs), flip-chip bonding techniques, or a combination of these capabilities.

The monolithic integration of CMOS-based circuitry and microneedle-based transducers solves several noteworthy challenges confronting those developing technologies in the medical devices and wearable sensors domains. The present invention represents a novel approach to facilitating the synthesis of a heterogeneous, self-contained sensor-transducer system that addresses the shortcomings of the prior art while remaining amenable to highly scalable manufacturing processes.

These prior art shortcomings include the following:

(1) The necessity of interconnect of distinct microneedle-based sensors and CMOS-based transducers, as required for the readout of said microneedles, by means of integration as discrete packaged and mounted/bonded devices populating a printed circuit board: Limitation: A printed circuit board containing discrete microneedle and CMOS systems cannot be easily miniaturized beyond the xy-dimensions associated with said systems as well as the interconnects between the two, thereby placing a technological barrier to the realization of miniaturized skin-worn sensor devices. Moreover, routing electrical connections between two or more such discrete systems on a printed circuit board imposes added constraints of complexity and cost. Mitigation: The utilization of advanced semiconductor processing and packaging techniques facilitates the creation of 2.5- or 3-dimensional, self-contained microneedle-CMOS sensor-transducer systems or heterogeneously integrated microneedle-CMOS architectures sharing a common substrate.

(2) The interconnect of discrete microneedle-based sensors and CMOS-based transducers using conventional PCB traces: Limitation: Interconnect of distinct microneedle and CMOS systems on a printed circuit board is not amenable to maintaining signal fidelity, especially when such signals are analog in nature and reside in the nanoampere/microvolt (or lower) range. Mitigation: As the spatial extent of the interconnect between two electronic systems is directly proportional to noise ingress, the co-location of microneedle and CMOS systems on a shared substrate or the interconnect of said systems by means of solder balls/wire bonds serves to minimize the distance over which said systems interact and hence the noise imparted in the combined system. By reducing interconnect length between the microneedle sensor and CMOS transducer, the chief source of electronic noise and signal degradation is thus minimized.

(3) Inability to scale heterogeneous microneedle- and CMOS-based systems to dimensions enabling unobtrusive, conformal, and flexible skin-adorned medical patches: Limitation: Owing to their disparate manufacturing and packaging requirements, silicon micro-fabricated microneedles and CMOS circuitry have conventionally been packaged as mutually-exclusive, discrete entities populating a printed circuit board. Indeed, heterogeneous integration in a single package or on a single substrate presents difficulty owing to incompatibilities in manufacturing processes and packaging requirements. Mitigation: Employing a monolithic approach to microneedle and CMOS integration, either by means of co-locating the said constituents on the same substrate, or packaging the components as a single stacked entity, heralds the realization of highly miniaturized, self-contained sensing systems capable of direct integration into skin-adorned medical patches characterized by low footprint.

The technology disclosed herein specifies methods to achieve the heterogeneous and monolithic integration of semiconductor-based solid microneedles sensor and the semiconductor-based CMOS circuitry transducer required to interpret readings from the sensor. The sensor preferably contains one or a plurality of solid microneedles on an anterior surface of a substrate, each containing an addressable sensing electrode. The sensor is preferably designed to penetrate a biological interface to access a physiological fluid or tissue. The transducer preferably contains one or a plurality of integrated circuits using complementary metal oxide semiconductor (CMOS) technology. The transducer is preferably designed to control the sensor by applying a specific signal or stimulus to the sensor as well as interpreting the resulting electrical response of the sensor to the signal or stimulus. The transducer preferably includes at least one of the following components: a potentiostat, an analog front end, an amplifier, a filter, an analog-to-digital converter, microcontroller, and a wireless radio. Three approaches may be leveraged to achieve this aim of heterogeneous integration of the sensor and the transducer.

The stacked substrate 10: The sensing electrodes are accessible on the opposing (posterior) surface of the substrate by means of vertically-oriented conducting channels known as through-substrate vias (TSVs), and as described in more detail in Windmiller, et al., U.S. patent application Ser. No. 15/913,709, filed on Mar. 6, 2018, for Methods For Achieving An Isolated Electrical Interface Between An Anterior Surface Of A Microneedle Structure And A Posterior Surface Of A Support Structure is hereby incorporated by reference in its entirety. At a location on a posterior surface in which the TSVs exit from the substrate, conductive pads are found to facilitate bonding to the surface of a second substrate. The conductive pads are preferably located on the posterior surface of the sensor, and are bonded to conductive pads on either the anterior or posterior surface of the transducer to facilitate an electrical communication between the sensor and the transducer. Bonding is achieved by at least one of: stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding. Optionally, the sensor and the transducer may be wire-bonded to achieve electrical interface between the two systems. Optionally, the transducer (following mating with the sensor) may be mated, in a similar fashion as above, to another CMOS-containing substrate. Optionally, the transducer (following mating with the sensor) may be wire-bonded or stud-bumped and soldered to a printed circuit board to enable electrical communication with discrete electrical or electronic devices such as, but not limited to, batteries, antennas, resistors, capacitors, inductors, diodes, transistors, and discrete semiconductor components.

The Co-Substrate Integration: The sensing electrodes are accessible on the opposing (posterior) surface of the substrate by means of vertically-oriented conducting channels known as through-substrate vias (TSVs). At a location on the posterior surface in which the TSVs exit from the substrate, conductive traces are found to route signals generated by the sensor to the transducer to facilitate an electrical communication between the sensor located on the anterior surface of substrate and the transducer located on the posterior surface of substrate. Optionally, the substrate (hereinafter referred to as the first substrate) may be mated to another CMOS-containing substrate (second substrate) such that the posterior surface of the first substrate (containing the transducer) is bonded to the anterior surface of the second substrate by means of at least one of: stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding. Optionally, the first substrate or the second substrate (if present) may be wire-bonded or stud-bumped and soldered to a printed circuit board to enable electrical communication with discrete electrical or electronic devices such as, but not limited to, batteries, antennas, resistors, capacitors, inductors, diodes, transistors, and discrete semiconductor components.

The Co-Planar Integration: The sensing electrodes are accessible on the same (anterior) surface of the substrate by means of horizontally-oriented conducting traces. The conductive traces route electrical signals generated by sensor to the transducer to facilitate an electrical communication between the sensor and the transducer, both co-located on spatially distinct regions on the anterior surface of the substrate. Optionally, the substrate (hereinafter referred to as the first substrate) may be mated to another CMOS-containing silicon die (second substrate) such that the posterior surface of the first substrate is bonded to the anterior surface of the second substrate by means of at least one of: stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding. Optionally, the first substrate or the second substrate may be wire-bonded or stud-bumped and soldered to a printed circuit board to enable electrical communication with discrete electrical or electronic devices such as, but not limited to, batteries, antennas, resistors, capacitors, inductors, diodes, transistors, and discrete semiconductor components.

Under each of the above scenarios, the substrate may comprise a semiconductor wafer or die selected from one of the Group IV elements (i.e. Silicon, Germanium), the Group VI elements (i.e. Selenium, Tellurium), composites comprising II-VI elements (i.e. Cadmium Sulfide, Zinc Oxide), and composites comprising III-V elements (i.e. Gallium Arsenide, Indium Phosphide); the TSV may comprise the doped or intrinsically conducting species of the above materials as well as a metal.

The microneedle sensor 5 breaches a biological interface to access a physiological fluid or tissue. The microneedle sensor 5 contains one or a plurality of solid microneedles on the anterior surface of a silicon substrate 10, each of the microneedle constituents contain an addressable sensing electrode in physical contact with the physiological fluid or tissue. In addition, the sensing electrode(s) are in direct electrical communication either with another region on the anterior surface of the silicon substrate (by means of metallic traces/conduits) or on the posterior surface of the substrate (by means of through-silicon vias 1). The microneedle sensor 5 is designed to stimulate, sustain, and provide a means to read out some electrophysiological or electrochemical signal or reaction at the electrode surface.

The CMOS transducer 30 converts some variations in electrophysiological or electrochemical quantities arising at the interface of the microneedle sensor 5 and the biological interface into an electrical signal or vice versa. The CMOS transducer 30 transduces the signal(s) produced by the microneedle sensor 5 to information capable of being interpreted to ascertain the level of some physiological or biochemical entity. The CMOS transducer 30 contains complementary metal oxide semiconductor circuitry, patterned on a silicon substrate, to implement at least one of the following functionalities: a potentiostat, an analog front end, an amplifier, a filter, an analog-to-digital converter, microcontroller, and a wireless radio. Optionally the CMOS transducer 30 can control the microneedle sensor 5 by applying a certain potential, current, or frequency-modulated signal while simultaneously quantifying the electrical response of the microneedle sensor 5. Optionally the CMOS transducer 30 can perform processing on the signal to mitigate noise and can feature a wireless capability to relay said raw or processed signal to another device. Optionally the CMOS transducer 30 can interface with a display to present the user with sensor readings.

The semiconductor substrates 10 provide a mechanical support for the implementation of sensor and transducer constituents. The semiconductor substrates 10 are comprised of a semiconductor wafer or die selected from one of the Group IV elements (i.e. Silicon, Germanium), the Group VI elements (i.e. Selenium, Tellurium), composites comprising II-VI elements (i.e. Cadmium Sulfide, Zinc Oxide), and composites comprising III-V elements (i.e. Gallium Arsenide, Indium Phosphide).

Through-substrate via 1 facilitate an electrical interconnect between anterior and posterior surfaces of a semiconductor substrate 10. The through-substrate vias 1 are comprised of a doped or intrinsically conducting species of the Group IV, Group VI semiconductor elements or binary semiconductor compounds comprising the II-VI and III-V elements. Optionally the through-substrate vias 1 may be comprised of a metal or metal alloy. In the case that the substrate 10 is comprised of silicon, this is also referred to as a through-silicon via 1.

Stud bumps/solder balls/epoxy 23 facilitate an electrical interconnect between two disparate substrates (silicon 10, PCB 35, or combination of the two).

Bond wire 50 facilitates an electrical interconnect between two disparate substrates (silicon 10, PCB 35, or combination of the two). The bond wire 50 is preferably comprised of a metal or metal alloy.

Figure 1:
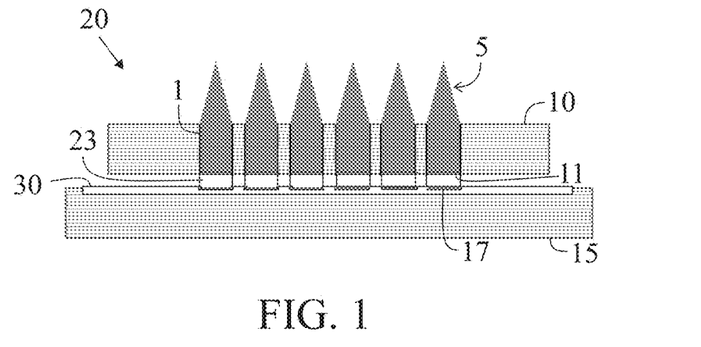
FIG. 1 is a diagrammatic representation of a die stack with CMOS circuitry on anterior surface of a second die.
Figure 1A:
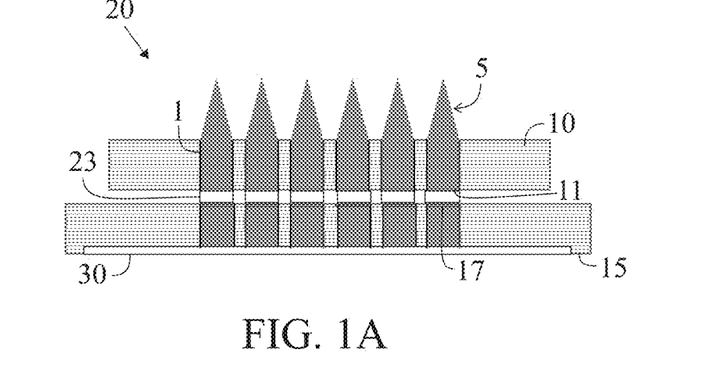
FIG. 1A is a diagrammatic representation of a die stack with CMOS circuitry on posterior surface of a second die.
Figure 1B:
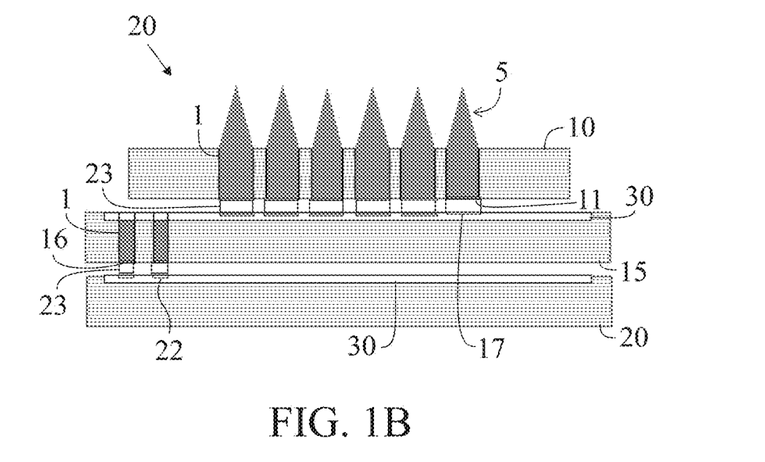
FIG. 1B is a diagrammatic representation of a die stack with CMOS circuitry on anterior surface of a second die and a third die.
Figure 1C:
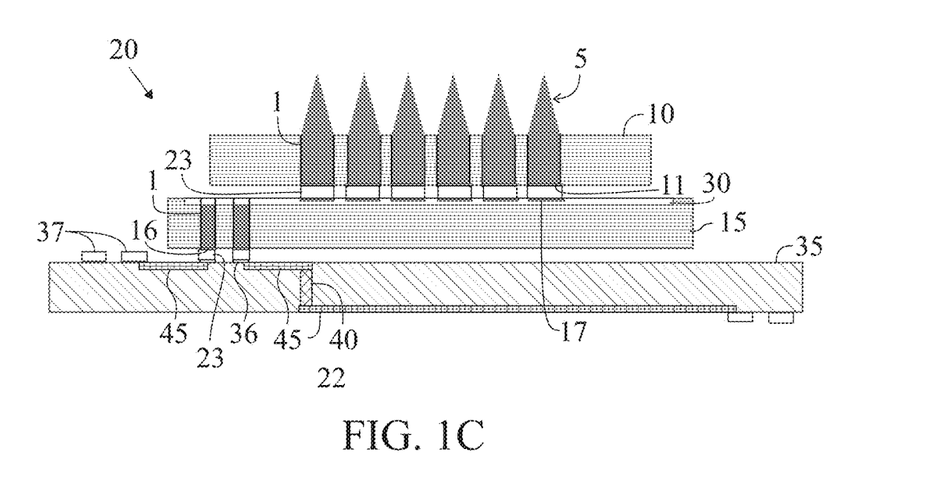
FIG. 1C is a diagrammatic representation of a die stack mounted on a printed circuit board containing assorted electrical circuit components, with CMOS circuitry on anterior surface of a second die.
Figure 1D:
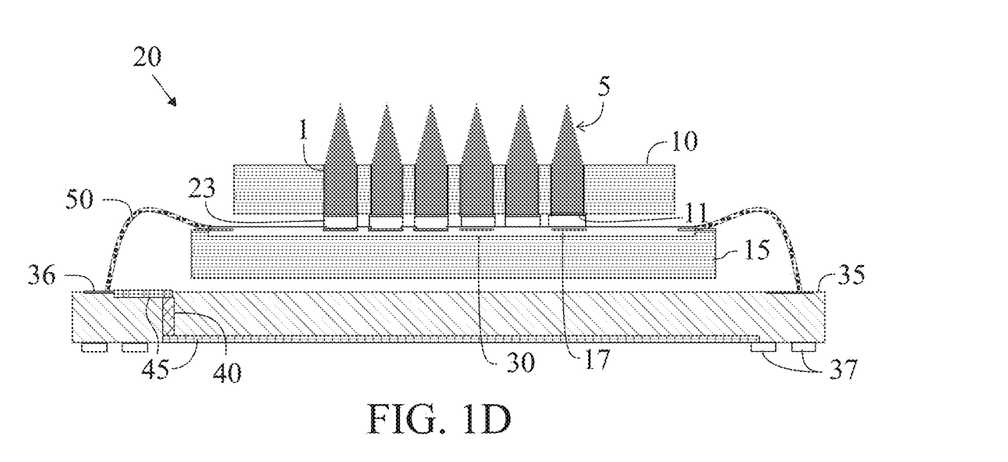
FIG. 1D is a diagrammatic representation of a die stack mounted on a printed circuit board containing assorted electrical circuit components, with CMOS circuitry on anterior surface of a second die.
Figure 1E:
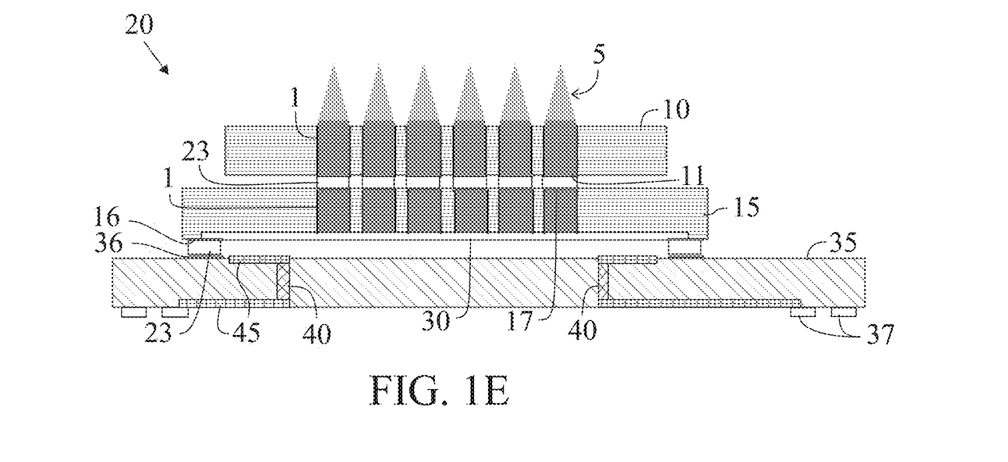
FIG. 1E is a diagrammatic representation of a die stack mounted on a printed circuit board containing assorted electrical circuit components, with CMOS circuitry on posterior surface of a second die.

FIGS. 1-1E illustrate diagrammatic representations of various die-stacking devices 20 that achieve heterogeneous integration of silicon-fabricated solid microneedle sensors and CMOS circuitry. FIG. 1 illustrates a skin-adorned physiological or biochemical sensing device 20 with a first die stack 10 with a CMOS circuitry 30 on an anterior surface of a second die 15. Each of the microneedles 5 is on a posterior pad 11 with stud bumps/sold balls/conductive epoxy 23 between the posterior pads 11 and anterior pads 17. FIG. 1A illustrates a first die stack 10 with CMOS circuitry 30 on posterior surface of second die 15, enabled by the presence of through-substrate vias 1. FIG. 1B illustrates a first die stack 10 with CMOS circuitry 30 on an anterior surface of a second die 15 and a third die 20, enabled by the presence of through-substrate vias 1 on the second die 15. FIG. 1C illustrates a first die stack 10, mounted on a printed circuit board ("PCB") 35 containing assorted electrical circuit components, with CMOS circuitry 30 on an anterior surface of a second die 15, enabled by the presence of through-substrate vias 1 on the second die 15. FIG. 1D illustrates a first die stack 10, mounted on a PCB 35 containing assorted electrical circuit components, with CMOS circuitry 30 on anterior surface of a second die 15, enabled by the presence of wire bonds 50 on the second die 15. FIG. 1E illustrates a die stack, mounted on a PCB 35 which comprises electrical circuit components 37 such as a potentiostat, an analog front end, an amplifier, a filter, an analog-to-digital converter, microcontroller, and a wireless radio, with CMOS circuitry 30 on a posterior surface of the second die 15, enabled by the presence of through-substrate vias 1 on both the second die 15 and PCB 35, and through anterior conductive pads 36 on the PCB 35, which are connected to posterior conductive pads 16 of the second die 15. A TSV 40 through the PCB 35 enables the connection to the electrical components 37 located on the posterior surface of the PCB 35.

Figure 2:
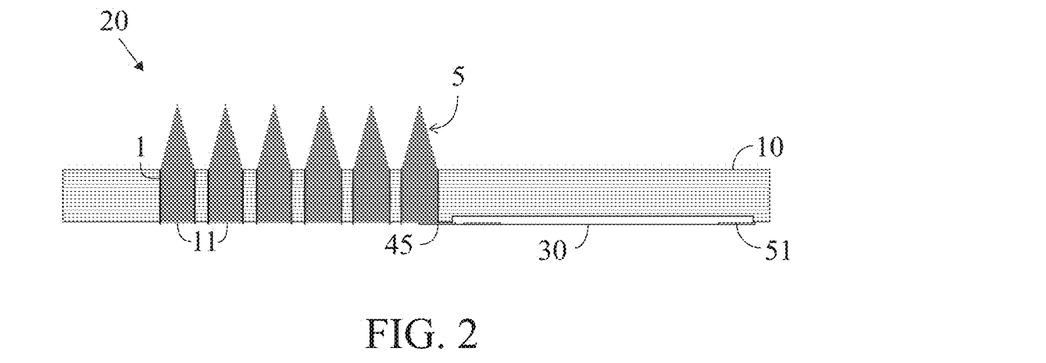
FIG. 2 illustrates microneedles on an anterior surface of die and CMOS circuitry on posterior surface of the die.
Figure 2A:
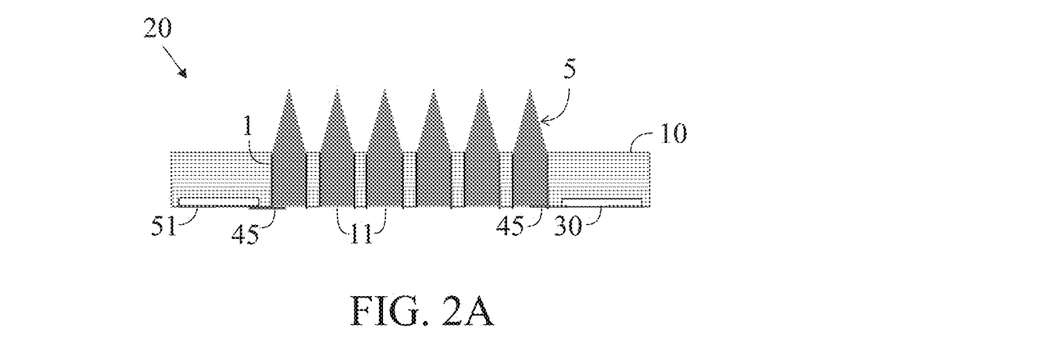
FIG. 2A illustrates microneedles on an anterior surface of die and CMOS circuitry on posterior surface of the die.
Figure 2B:
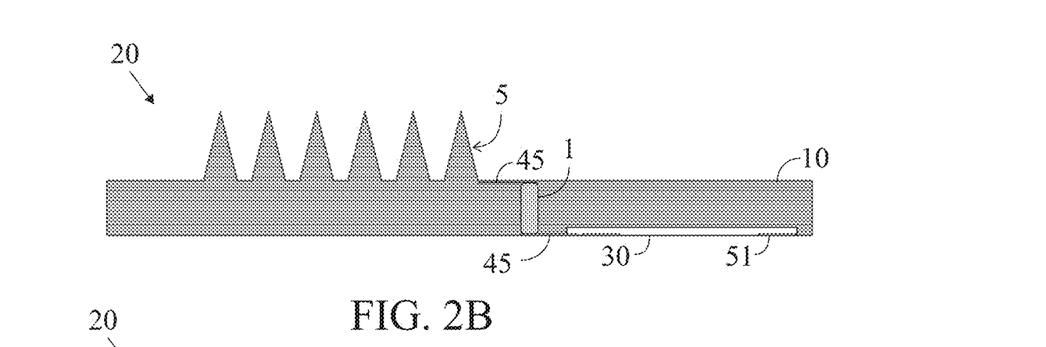
FIG. 2B illustrates microneedles on an anterior surface of die and CMOS circuitry on posterior surface of said die.
Figure 2C:
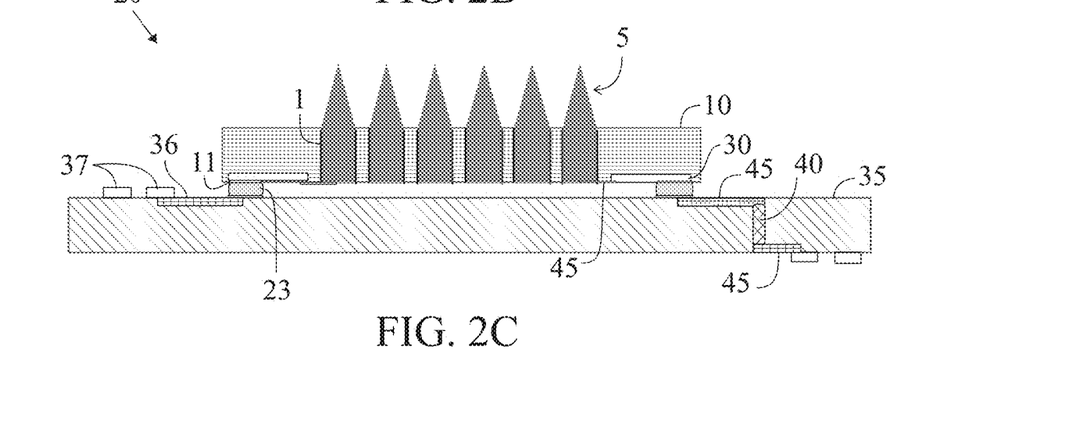
FIG. 2C illustrates microneedles on an anterior surface of die and CMOS circuitry on posterior surface of said die.

FIGS. 2-2C illustrate diagrammatic representations of various co-substrate devices 20 that achieve heterogeneous integration of silicon-fabricated solid microneedle sensors and CMOS circuitry. As shown in FIGS. 2 and 2A, microneedles 5 are positioned on an anterior surface of die 10 with CMOS circuitry 30 on a posterior surface of the die 10, and an interconnect between the microneedles 5 and the CMOS circuitry 30 is enabled by the presence of through-substrate vias 1 positioned colinearly with the microneedles 5 and a conductive trace 45. A bonding pad 51 is positioned on the CMOS circuitry 30. Posterior pads 11 are positioned below the microneedles 5. As shown in FIG. 2B, microneedles 5 are positioned on an anterior surface of a die 10 with CMOS circuitry 30 on a posterior surface of the die 10, and an interconnect is enabled by the presence of through-substrate vias 1 positioned in a spatially distinct region from the microneedles 5. As shown in FIG. 2C, the microneedles 5 are positioned on an anterior surface of a die 10 with CMOS circuitry 30 on a posterior surface of the die 10, and an interconnect is enabled by the presence of through-substrate vias 1 positioned colinearly with the microneedles 5, and the die 10 is mounted on a PCB 35 which comprises electrical circuit components 37 such as a potentiostat, an analog front end, an amplifier, a filter, an analog-to-digital converter, microcontroller, and a wireless radio, with an electrical interconnect achieved between the die 10 and the PCB 35 by means of stud bumps 23, solder balls 23, and/or conductive epoxy 23, and with an anterior conductive pad 36. A TSV 40 connects traces 45 on the anterior surface and posterior surface of the PCB 35.

Figure 3:
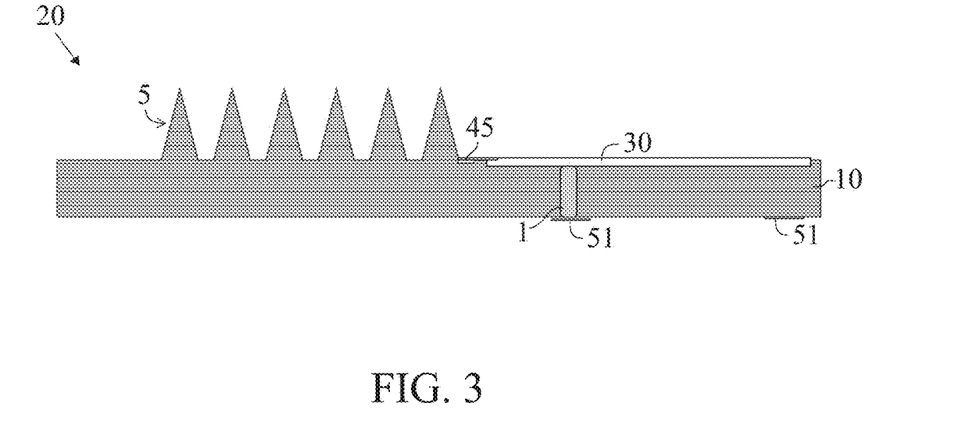
FIG. 3 illustrates microneedles and CMOS circuitry co-located on an anterior surface of die in spatially distinct regions.
Figure 3A:
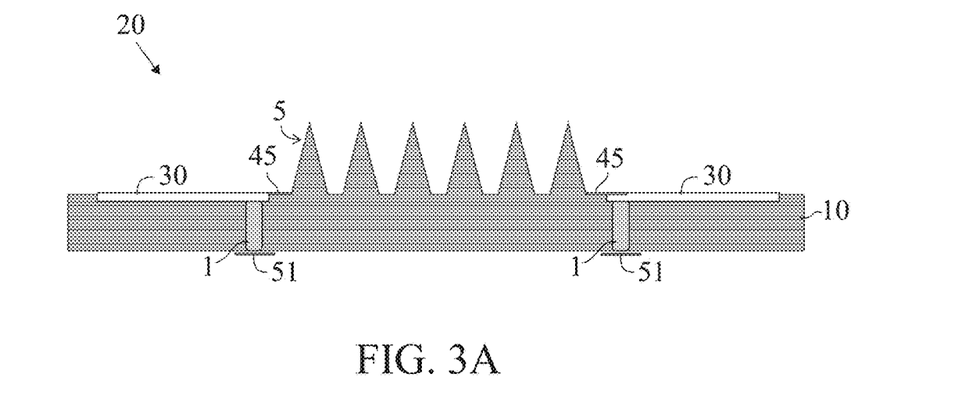
FIG. 3A illustrates microneedles and CMOS circuitry co-located on an anterior surface of die in spatially distinct regions.
Figure 3B:
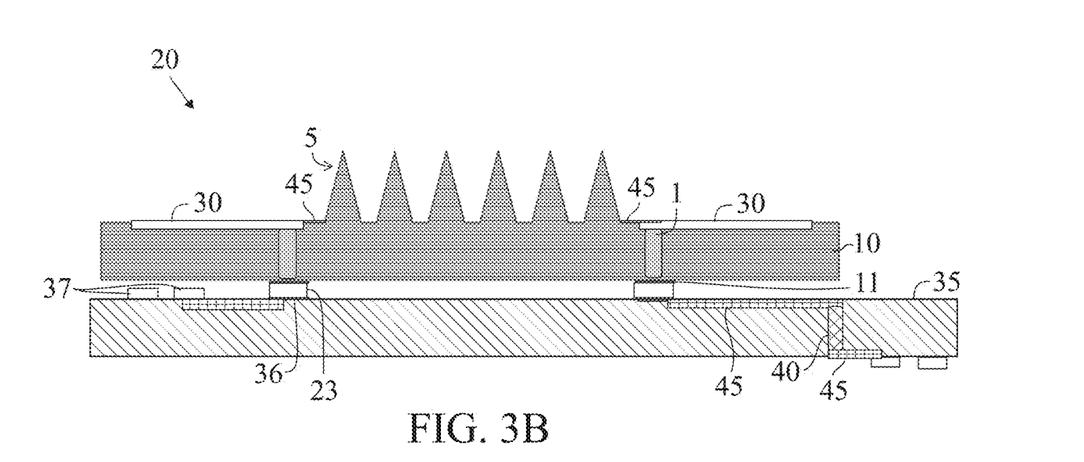
FIG. 3B illustrates microneedles and CMOS circuitry co-located on an anterior surface of die in spatially distinct regions.

FIGS. 3-3B illustrate diagrammatic representations of various co-planar devices 20 that achieve heterogeneous integration of silicon-fabricated solid microneedle sensors and CMOS circuitry. As shown in FIGS. 3 and 3A, microneedles 5 and CMOS circuitry 30 are co-located on an anterior surface of a die 10 in spatially distinct regions, and interconnects between the microneedles 5 and the CMOS circuitry 30 are enabled by the presence of conductive traces 45 positioned co-planarly with the CMOS circuitry 30. Anterior bonding pads 51 are on an anterior surface of the die 10. A TSV 1 connects the CMOS circuitry 30 to the anterior bonding pad 51. As shown in FIG. 3B, microneedles 5 and CMOS circuitry 30 are co-located on an anterior surface of a die 10 in spatially distinct regions, and interconnects between the microneedles 5 and the CMOS circuitry 30 are enabled by the presence of conductive traces 45 positioned co-planarly with the CMOS circuitry 30. The die 10 is mounted on a PCB 35 which comprises electrical circuit components 37 such as a potentiostat, an analog front end, an amplifier, a filter, an analog-to-digital converter, microcontroller, and a wireless radio. An electrical interconnect is achieved between the die 10 and the PCB 35 by means of through-substrate vias 1 in conjunction with stud bumps 23, solder balls 23, and/or conductive epoxy 23, and with an anterior conductive pad 36. A TSV 40 connects traces 45 on the anterior surface and posterior surface of the PCB 35.

One embodiment is a skin-adorned physiological or biochemical sensing device 20. The device 20 comprises a first substrate 10 and a second substrate 15. The first substrate 10 comprises an anterior surface and a posterior surface. The first substrate 10 comprises an array of solid microneedles 5 on the anterior surface designed to penetrate a biological interface to access a physiological fluid or tissue. Each microneedle 5 contains an addressable metal electrode located on the surface of the microneedle 5 which is in electrical communication with a metal surface located on the posterior surface of the first substrate 10 by means of a conductive conduit 1, to form a microneedle sensor component 5 capable of electrical interface with the physiological fluid or tissue. The conductive conduit 1 preferably comprises at least one of a through-substrate via 1. The through-substrate via 1 is preferably comprised of a doped or intrinsically conducting semiconductor; said semiconductor includes at least one of silicon, germanium, silicon germanium, gallium arsenide, indium phosphide, gallium nitride, zinc oxide, and cadmium selenide. The second substrate 15 has an anterior and a posterior surface. The second substrate 15 comprises integrated circuitry 30 on the anterior surface designed to transduce at least one signal produced by an electrophysiological or electrochemical reaction occurring at the metal electrode, to form a transducer component. The posterior surface of the first substrate 10 is stacked to the anterior surface of the second substrate 15. The first substrate 10 is bonded to the second substrate 15 to create an electrical interconnect between the first substrate 10 and the second substrate 15. A sensing device 20 is formed that is capable of interpreting the signal arising from the electrophysiological or electrochemical reaction to ascertain the level of some physiological or biochemical entity.

The first substrate is preferably a semiconductor that includes at least one of silicon, germanium, silicon germanium, gallium arsenide, indium phosphide, gallium nitride, zinc oxide, and cadmium selenide.

The electrical interface preferably includes at least one of applying an electrical stimulus to said physiological fluid or tissue and detecting an electrical signal arising within said physiological fluid or tissue. The electrical stimulus includes at least one of a DC voltage, DC current, AC voltage, AC current, frequency-modulated signal, amplitude-modulated signal, or phase-modulated signal. The electrical signal includes at least one of a DC voltage, DC current, AC voltage, AC current, frequency-modulated signal, amplitude-modulated signal, or phase-modulated signal.

The integrated circuitry 30 preferably comprises at least one of a potentiostat, an analog front end, an amplifier, a filter, an analog-to-digital converter, microcontroller, and a wireless radio.

The bonding means is at least one of stud bumps, solder balls, direct bonding, surface activated bonding, plasma activated bonding, fusion bonding, metal layer bonding, anodic bonding, eutectic bonding, glass frit bonding, insulating layer bonding, adhesive bonding, thermocompression bonding, reactive bonding, transient liquid phase diffusion bonding, physical bonding, and chemical bonding.

The second substrate 15 is further attached to a PCB 35 by means of at least one of: wire bonds 50, stud bumps 23, and solder balls 23.

The PCB 35 preferably comprises discrete electrical or electronic devices such as, but not limited to, batteries, antennas, resistors, capacitors, inductors, diodes, transistors, and discrete semiconductor components.

McCanna et al., U.S. patent application Ser. No. 14/843,926, filed on Sep. 2, 2015, for a Miniaturized Sub-Nanoampere Sensitivity Low-Noise Potentiostat System is hereby incorporated by reference in its entirety.

Windmiller et al., U.S. patent application Ser. No. 14/955,850, filed on Dec. 1, 2015, for a Method And Apparatus For Determining Body Fluid Loss is hereby incorporated by reference in its entirety.

Windmiller, U.S. patent application Ser. No. 15/177,289, filed on Jun. 8, 2016, for a Methods And Apparatus For Interfacing A Microneedle-Based Electrochemical Biosensor With An External Wireless Readout Device is hereby incorporated by reference in its entirety.

Wang et al., U.S. Patent Publication Number 20140336487 for a Microneedle Arrays For Biosensing And Drug Delivery is hereby incorporated by reference in its entirety.

Windmiller, U.S. patent application Ser. No. 15/590,105 for a Tissue-Penetrating Electrochemical Sensor Featuring A Co Electrodeposited Thin Film Comprised Of A Polymer And Bio-Recognition Element is hereby incorporated by reference in its entirety.

Windmiller, et al., U.S. patent application Ser. No. 15/913,709, filed on Mar. 6, 2018, for Methods For Achieving An Isolated Electrical Interface Between An Anterior Surface Of A Microneedle Structure And A Posterior Surface Of A Support Structure is hereby incorporated by reference in its entirety.

PCT Application Number PCT/US17/55314 for an Electro Deposited Conducting Polymers For The Realization Of Solid-State Reference Electrodes For Use In Intracutaneous And Subcutaneous Analyte-selective Sensors is hereby incorporated by reference in its entirety.

From the foregoing it is believed that those skilled in the pertinent art will recognize the meritorious advancement of this invention and will readily understand that while the present invention has been described in association with a preferred embodiment thereof, and other embodiments illustrated in the accompanying drawings, numerous changes modification and substitutions of equivalents may be made therein without departing from the spirit and scope of this invention which is intended to be unlimited by the foregoing except as may appear in the following appended claim. Therefore, the embodiments of the invention in which an exclusive property or privilege is claimed are defined in the following appended claims.

We claim as our invention the following:

1. A skin-adorned sensing device, comprising:
a first substrate comprising:
an anterior surface comprising an array of microneedles configured to sense an electrophysiological or electrochemical reaction within physiological fluid or tissue, wherein each microneedle of the array of microneedles comprises an addressable electrode located on a surface of the microneedle;
a posterior surface comprising a first conductive pad; and
a first conductive conduit extending through the first substrate and configured to provide electrical communication between the addressable electrode of a first microneedle of the array of microneedles and the first conductive pad;
a second substrate comprising:
a second conductive pad in electrical communication with the first conductive pad of the first substrate;
a third conductive pad positioned posterior to the second conductive pad; and
a second conductive conduit extending through the second substrate and configured to provide electrical communication between the second conductive pad and the third conductive pad,
wherein a posterior surface of the second substrate comprises a CMOS circuitry transducer; and
a printed circuit board comprising an anterior conductive pad, the anterior conductive pad in electrical communication with the third conductive pad of the second substrate.

2. The device of claim 1, wherein one or both of the first conductive conduit and the second conductive conduit comprises a through-substrate via.

3. The device of claim 1, wherein the CMOS circuitry transducer comprises one or more of: a potentiostat, a galvanostat, an analog front end, an amplifier, a filter, an analog-to-digital converter, a microcontroller, and a wireless radio.

4. The device of claim 1, wherein the first substrate and the second substrate are bonded by solder.

5. The device of claim 1, wherein the first substrate and the second substrate are bonded by solder and epoxy.

6. The device of claim 1, wherein the printed circuit board further comprises:
one or more electrical circuit components on a posterior surface of the printed circuit board; and
a through substrate via between the anterior conductive pad of the printed circuit board and the one or more electrical circuit components.

7. The device of claim 6, wherein the one or more electrical circuit components comprise one or more of a potentiostat, an analog front end, an amplifier, a filter, an analog-to-digital converter, microcontroller, a wireless radio, a battery, and an antenna.

8. The device of claim 1, wherein the second substrate is bonded to the printed circuit board by stud bumps.

9. The device of claim 1, wherein the array of microneedles is configured to penetrate a user's skin to access the physiological fluid or tissue.

10. The device of claim 1, wherein the device is configured to interpret a signal produced by the electrophysiological or electrochemical reaction occurring at the array of microneedles to determine a level of a physiological or biochemical entity.

11. A skin-adorned sensing device comprising:
a die stack mounted on a printed circuit board, the die stack comprising:
a first substrate comprising:
an array of microneedles configured to sense an electrophysiological or electrochemical reaction within physiological fluid or tissue; and
a first conductive conduit in electrical communication with a first microneedle of the array of microneedles and extending through the first substrate; and
a second substrate comprising:
a second conductive conduit extending through the second substrate and longitudinally aligned with the first conductive conduit, wherein the first conductive conduit and the second conductive conduit are configured to provide electrical communication between the first microneedle of the array of microneedles and the printed circuit board, wherein a posterior surface of the second substrate comprises a CMOS circuitry transducer; and wherein the device is configured to interpret a signal produced by an electrophysiological or electrochemical reaction occurring at the first microneedle of the array of microneedles to determine a level of a physiological or biochemical entity.

12. The device of claim 11, wherein one or both of the first conductive conduit and the second conductive conduit comprise a through-substrate via.

13. The device of claim 12, wherein the through-substrate via comprises one or more of silicon, germanium, silicon germanium, gallium arsenide, indium phosphide, gallium nitride, zinc oxide, and cadmium selenide.

14. The device according to claim 11, wherein the printed circuit board comprises electrical circuit components configured to perform the interpreting and the determining, the electrical circuit components comprising one or more of a potentiostat, an analog front end, an amplifier, a filter, an analog-to-digital converter, microcontroller, and a wireless radio.

15. The device of claim 14, wherein the die stack is mounted to an anterior surface of the printed circuit board, and wherein the electrical circuit components are on a posterior surface of the printed circuit board.

16. The device of claim 15, wherein an electrical connection between the die stack and the printed circuit board is formed by an anterior conductive pad positioned on the anterior surface of the printed circuit board.

17. The device of claim 14, wherein the printed circuit board comprises a through-substrate via that provides electrical communication between the die stack and the electrical circuit components.

18. The device of claim 11, wherein the device is further configured to apply an electrical stimulus to the physiological fluid or tissue to sustain the electrophysiological or electrochemical reaction.

19. A method for quantifying a physiological or biochemical entity in a physiological fluid or tissue, the method comprising:

providing a die stack mounted on a printed circuit board, the die stack comprising:
a first substrate comprising:
an anterior surface comprising an array of microneedles configured to sense an electrophysiological or electrochemical reaction within physiological fluid or tissue; and
a first conductive conduit in electrical communication with a first microneedle of the array of microneedles and extending through the first substrate; and
a second substrate comprising:
a second conductive conduit extending through the second substrate and longitudinally aligned with the first conductive conduit,
wherein the first conductive conduit and the second conductive conduit are configured to provide electrical communication between the first microneedle of the array of microneedles and the printed circuit board, and
wherein a posterior surface of the second substrate comprises a CMOS circuitry transducer;

penetrating a biological interface with the array of microneedles;

routing a signal produced by an electrophysiological or electrochemical reaction within the physiological fluid or tissue from a first microneedle of the array of microneedles to a printed circuit board via the first conductive conduit, the CMOS circuitry transducer, and the second conductive conduit; and interpreting the signal with the printed circuit board to determine a level of the physiological or biochemical entity.

20. The method of claim 19, further comprising applying an electrical stimulus to the physiological fluid or tissue with the first microneedle of the array of microneedles.

21. The method of claim 20, further comprising sustaining the electrophysiological or electrochemical reaction within the physiological fluid or tissue by continuously applying the electrical stimulus.

\* \* \* \* \*